Figure 1:
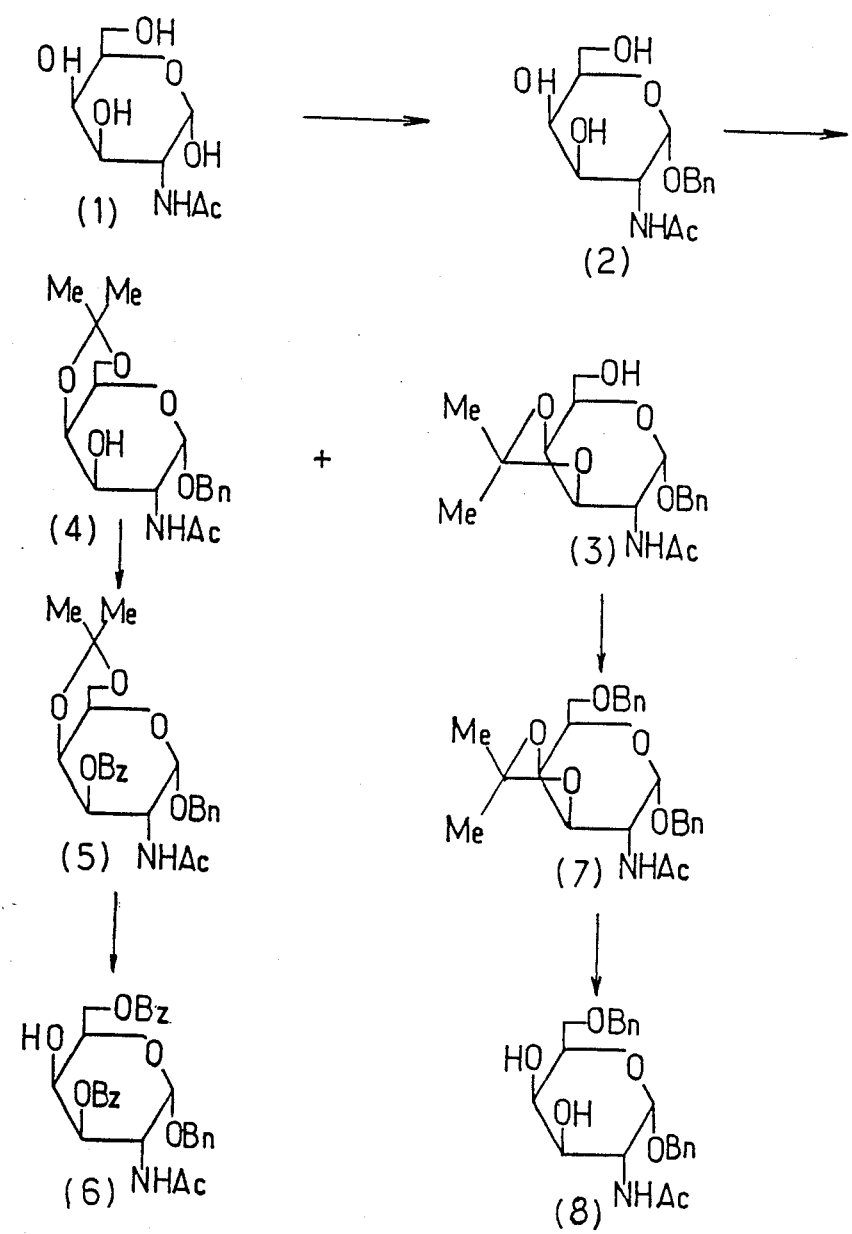

United States Patent [19]
Jacquinet et al.

[11] Patent Number: 4,943,630
[45] Date of Patent: * Jul. 24, 1990

[54] METHOD FOR CARRYING OUT THE ORGANIC SYNTHESIS OF OLIGOSACCHARIDES CONTAINING GALACTOSAMINE-URONIC ACID PATTERNS, NEW OLIGOSACCHARIDES OBTAINED AND BIOLOGICAL APPLICATIONS THEREOF

[75] Inventors: Jean-Claude Jacquinet, Orleans-La Source; Maurice Petitou, Paris; Pierre Sina, Orleans; Jean Choay, Paris, all of France

[73] Assignee: Choay, S.A., Paris, France

[*] Notice: The portion of the term of this patent subsequent to Aug. 19, 2003 has been disclaimed.

[21] Appl. No.: 856,855

[22] Filed: Apr. 21, 1986

Related U.S. Application Data

[63] Continuation of Ser. No. 624,628, filed as PCT FR83/00217 on Oct. 27, 1983, published as WO84/01777 on May 10, 1984, abandoned.

[30] Foreign Application Priority Data

Oct. 27, 1982 [FR] France ................. 82 18003

[51] Int. Cl.$^5$ ................. A61K 31/70; C07H 5/06
[52] U.S. Cl. ................. 536/123; 536/21; 536/4.1; 536/18.5; 536/18.6; 536/124
[58] Field of Search ................. 536/123, 18.5, 18.6, 536/4.1, 21, 124; 514/53

[56] References Cited

U.S. PATENT DOCUMENTS

| | | | |
|---|---|---|---|
| 4,435,387 | 3/1984 | Schaub et al. | 536/18.5 |
| 4,607,025 | 8/1986 | Petitou et al. | 514/53 |

FOREIGN PATENT DOCUMENTS

| | | |
|---|---|---|
| 0014184 | 8/1980 | European Pat. Off. |
| 0027089 | 4/1981 | European Pat. Off. |
| 0048231 | 3/1982 | European Pat. Off. |
| 0064012 | 11/1982 | European Pat. Off. |
| 0084999 | 8/1983 | European Pat. Off. |

OTHER PUBLICATIONS

Tetrahedron Letters, No. 5, Klemer, pp. 431–433, 1972.
Tetrahedron Letters, No. 30, Kiss and Wyss, pp. 3055–3058, 1972.
Carbohydrate Research, vol. 105, No. 1, Ogamo et al., Jul. 7, 1982.
Carbohydrate Research, vol. 103, No. 1, Seno, May 1, 1982.
Carbohydrate Research, vol. 78, No. 2, Klein, Jan. 15, 1980.
Carbohydrate Research, vol. 87, No. 2, Ayotte et al., Dec. 15, 1980.
Bulletin de la Societe de Chimie Biloqique, Tome XLII, 1960, Nos. 9–10, Barker et al., 25 Jan. 1961.
Helvetica Chimica Acta, H. C. A. vol. 58, Fascs 6, Wyss et al., pp. 1847–64 *The Journal of Biochemistry, vol. 92, No. 1,* Kosoia, Jul. 1982.
IUPAC Pure & Applied Chemistry, vol. 50, Sinay, pp. 1437–1452.
Angewandte Chemie, vol. 21, No. 3, Paulsen, Mar. 1982, pp. 155–224.
Organic Chemistry, 2nd Ed., Louis F. Fieser & Mary Fieser, pp. 229–231.
Methods in Carbohydrate Chemistry, vol. VIII, 1980, Marthorpe, pp. 305–311.
Clinica Chemica Acta, 123, Hopwood, pp. 241–250, 8/82.

*Primary Examiner*—Ronald W. Griffin
*Attorney, Agent, or Firm*—Davis, Hoxie, Faithfull & Hapgood

[57] ABSTRACT

Novel processes for synthesizing acid mucopolysaccharide fragments having from 2–12 saccharides and substantially pure products of a single structure produced thereby. Condensation are disclosed between a first protected saccharide and a second protected saccharide to form a protected condensation product having units linked in the manner found in chondroitin sulfate and dermatan sulfate and having protecting groups thereon which allow selective positioning of functional groups, in particular sulfate, at desired positions. Other condensations are disclosed in which a protected condensation product is formed which can be elongated, and has protecting groups thereon which allow selective positioning of functional groups, in particular sulfate, at desired positions. Also disclosed is a process for selectively positioning functional groups on a protected acid mucopolysaccharide having from 2–12 units.

53 Claims, 9 Drawing Sheets

(8) → (9) + (10)

→ (11) +

(12)

(13) (14) (15)

(16) (17) (18)

(19) (20)

(21) (22)

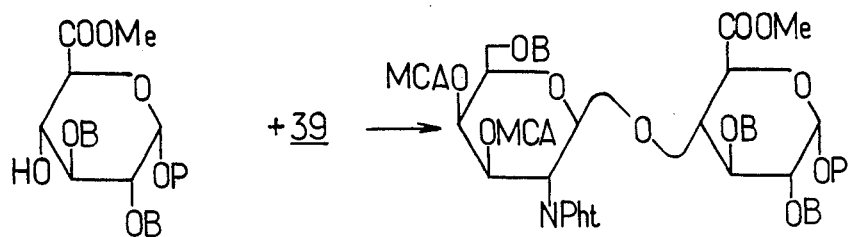
(44)        (46)
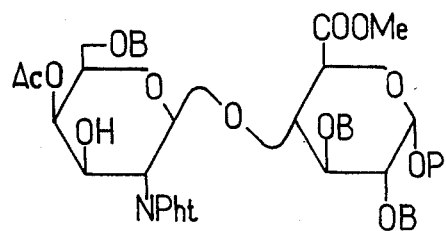
(47)
Fig.8.
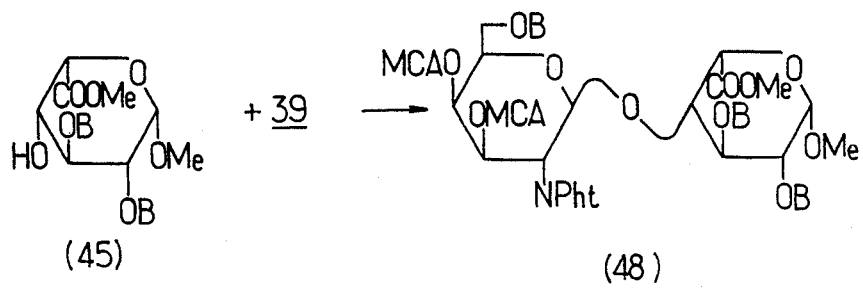
(45)        (48)
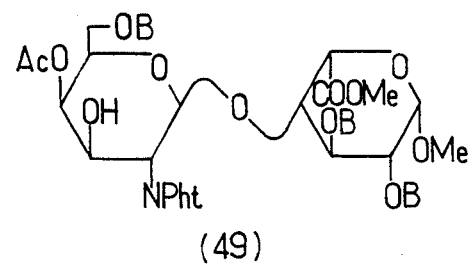
(49)

27 + 44 ⟶

(50)

⟶

(51)

(52)       (53)

(54)

54 + 44 ⟶

(55)

54 + 43 ⟶

(56)

METHOD FOR CARRYING OUT THE ORGANIC SYNTHESIS OF OLIGOSACCHARIDES CONTAINING GALACTOSAMINE-URONIC ACID PATTERNS, NEW OLIGOSACCHARIDES OBTAINED AND BIOLOGICAL APPLICATIONS THEREOF

This application is a continuation of application Ser. No. 624,628, filed as PCT FR83/00217 on Oct. 27, 1983 published as WO84/01777 on May 10, 1984, now abandoned.

The invention relates to a process for the organic synthesis of oligosaccharides constituting or comprising fragments of acid mucopolysaccharides. It also relates to the synthesis of derivatives of these oligosaccharides.

The invention relates, in addition, to novel oligosaccharides of the above-indicated type and to their derivatives, possessing, particularly, biological properties conferring on them, in particular, interest as medicaments and/or useful, for example, as laboratory reagents.

It is directed also to their uses particularly their biological and biochemical uses.

By the term "acid mucopolysaccharide", is meant derivatives also currently called glycosaminoglycuronoglycanes. It concerns oligosaccharides and polysaccharides encountered more especially in chains of biologically active derivatives such as derivatives of dermatane-sulphate, chondroitins, chondrosine and chondroitin-sulphates.

In natural products, the mucopolysaccharides concerned are essentially formed of alternate amino-sugar-uronic acid units, or conversely. In these units, the amino-sugar, denoted below by A, has more especially a D-glucosamine structure. The uronic acid, which will be called U, has, more especially, a D-glucuronic acid or L-iduronic acid structure.

The basic structures for A and U correspond respectively to the formulae x, y and z below:

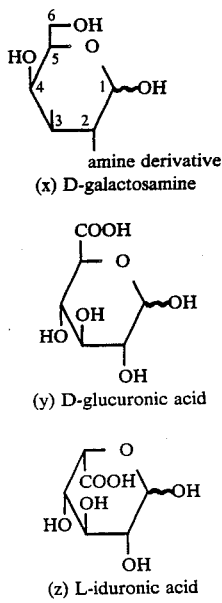

(x) D-galactosamine amine derivative (y) D-glucuronic acid (z) L-iduronic acid

In the natural products concerned, these various units are linked to one another stereo-specifically generally by

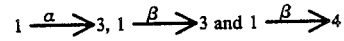

linkages.

In chondroitins and chondroitin-sulphates, there are encountered linkages of the

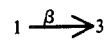

type (between the y and x units) and of the

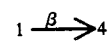

type (between the x and y units).
Linkages of the

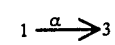

type (between z and x units) and of the

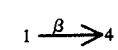

type (between the x and z units) exist, in addition, in dermatane-sulphate.

It will be noted, also, still with reference to natural products, that the above units comprise specific substitutions, that is to say certain substitutions at given positions. The chains of natural products contain, thus, for example, —O-substituted units, 4 or 6, or 4,6-disulphate-D-galactosamine and non-O-substituted units, like, for example, units D-glucuronic acid, L-iduronic acid and D-galactosamine. In addition, the unit x is N-substituted at the 2 position by -N-acetyl groups.

The importance of the therapeutic uses of the above acid mucopolysaccharides is known, in particular, for the prevention and treatment of disorders of cloting and of the vascular wall, and in particular thromboses and atheroscleroses and arterioscleroses or to combat aging of the tissues, or degenerative type manifestations, such as alopecia.

The methods proposed until now to obtain this type of product bring into play extraction techniques from natural sources for example from animal organs.

The progress of the researches of applicants in this field has led them to investigate novel means enabling this type of product to be obtained and more especially study of the possibilities of obtaining them synthetically.

In this respect, it is appropriate to measure the number of problems raised by such synthesis. In fact, on the one hand, these products contain in their chains several types of A and U units. On the other hand, some linkages between these units correspond to a given stereochemistry and are of the 1,4 type, of which the particular difficulties of production are well-known. In addition, each unit comprises one or several specific substitutions according to the type of product concerned.

It follows that such syntheses have practically never been contemplated until now in the scientific literature, more particularly, as regards L-iduronic acid.

All these elements highlight the restrictive requirements of which it is easy to appreciate the difficulties that they involve for the development of a general process and of the process of synthesis.

By researching conditions of oside synthesis suitable for the development of this type of compound, Applicants have developed a strategy by selecting certain particular types of protection for the substances utilised.

The work carried out has then shown that with such so-protected substances, it was possible to produce a stereo-specific chain formation and then to introduce, if desired, into the sequences formed, given substitutions at predetermined positions.

According to one aspect presenting an interest of which the importance will be measured, the process developed has great flexibility. It is thus possible to arrive at, with the advantages in particular of specificity and purity associated with a synthetic process, numerous oligosaccharide derivatives including the specific substitutions encountered with natural products, or even different substitutions and/or again units of similar structure with different configurations.

Due to this process, applicants have obtained oligosaccharides endowed with properties of great value. The process of the invention also permits access to a large number of particularly valuable oligosaccharides, in particular for biological reagents and/or for reference compounds for structure studies.

It is therefore an object of the invention to provide a process for producing, synthetically, oligosaccharides and their derivatives or the like, including or corresponding to fragments of acid mucopolysaccharides.

It is also an object to provide means enabling the establishment between A and U type units of glycoside linkages in the desired stero-specificity.

It is also an object to provide means enabling the introduction into the units of the glycoside chain of given functional groups, in particular of specific substituents such as encountered in the chains of biologically active molecules, particularly those of the dermatane-sulphate, chondroitin-sulphate, or chondroitin type.

It is also an object to provide means enabling the production of oligosaccharides such as mentioned above, but of which the substituents and/or the chemical nature of the sugars and/or the position and configuration of the inter-glycoside linkages and/or the configuration of the monosaccharides and/or the order of the enchainments are different from those of natural products.

According to another aspect, it is also an object of the invention to provide novel oligosaccharides constituting intermediate products of the process of synthesis concerned in which all the —OH groups of the various units are blocked by protective groups and the precursor groups of the functional radicals possibly present; if necessary, these radicals themselves are also protected.

According to yet another aspect, the invention is aimed at providing novel oligosaccharides having the structure of the above natural products as well as oligosaccharides corresponding to fragments of these products.

It is also directed at providing novel oligosaccharides possessing specific substitutions of natural products.

It is also an object of the invention to provide novel oligosaccharides bearing substitutions different from the specific substitutions concerned and/or including different units with respect to the natural products considered above.

The invention also relates to the biological uses of these oligosaccharides, particularly as active medicinal substances, laboratory agents or reference substances for the study, in particular, of compounds including this type of structure.

The process of synthesis of the invention is characterised in that it brings about the reaction of two compounds:

constituted or terminated respectively by A units of galactosamine structure, in particular D-galactosamine, and U units of glucuronic acid structure, in particular D-glucuronic, or iduronic acid, in particular L-iduronic acid;

one of the units A or U being an alcohol in which the —OH group of the alcohol function occupies any one of the positions 3, 4 or 6 in the case of unit A and 2, 3 or 4 in the case of unit U, the other unit possessing an activated anomeric carbon, that is to say comprising a reactive group capable of establishing with the —OH group of the alcohol the desired glycosylation —O— linkage, in the desired stereo-chemistry, to form a —A—U or —U—A sequence;

the reactive group of A and U being compatible with the protective groups and/or functional groups present on the units;

all the position of A and U excepted those of which the anomeric carbon is activated bearing —OH, amino or carboxyl groups, or precursors of such groups, the groups themselves, when they are present being blocked by one or advantageously several types of protective groups, these various groups being compatible with one another and with the above precursors, these protective groups and precursors being inert with respect to the glycosylation reaction and with the reactive groups, permitting the positioning, in the course of subsequent operations, of given substituents at the various positions, and this, as the case may be, sequentially, the conditions of application to cause the starting substances to react being selected so as not to alter the structure of the units of these substances and the nature of the various substituents present.

Due to the above arrangements, it is thus possible to form a covalent bond between the units of structure A and U and this, in the stereo-chemistry which this type of enchainment presents in the biologically active molecules already considered.

It is even possible by means of the invention to carry out the desired chain formations in a given order and/or possessing a given stereo-specificity.

The means proposed according to the invention thus enable the establishment particularly of a

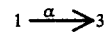

type linkage between a L-iduronic acid unit and a D-galactosamine unit, a

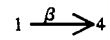

type linkage between a D-galactosamine unit and either a D-glucuronic acid unit or a L-iduronic acid unit and a

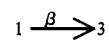

type linkage between a D-glucuronic acid unit and a D-galactosamine unit.

The mono- or oligo-saccharidic intermediates of this synthesis are semi-open or open products. A compound will be called semi-open on the right when it is a compound activated or potentially activatable on its anomeric carbon, thus permitting its transfer to the non-reducing end of a monosaccharide or of an oligosaccharide. The expression "compound semi-open on the left" will denote a monosaccharide or an oligosaccharide possessing a single free or potentially free —OH function, enabling its specific glycosylation. By way of illustration, there is indicated below the formula 1 of an example of a compound semi-open on the left and that 2 of an example of a compound semi-open on the right:

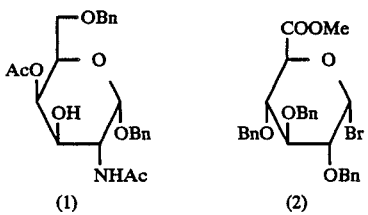

wherein Ac represents an acetyl group, Bn a benzyl group and Me a methyl group.

It follows that derivatives will be called open when they relate to a derivative semi-open both on the right and on the left according to the above definition, such derivatives permitting elongation of the chain in both directions. A derivative of this type corresponds for example to formula 3:

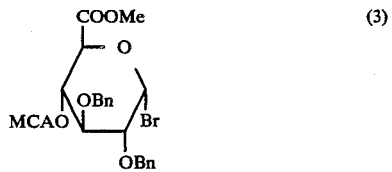

wherein Bn and Me are as defined above and MCAO represents a monochloroacetyl group.

As for closed derivatives, they are substances whose units cannot give rise to chain elongation by reason of the nature of their substituents.

According to an additional feature to be able to add units to the A—U or U—A sequence formed in the preceding step, the A and U units of the sequence formed must include temporary protective groups, that is to say groups capable of selectively blocking a position of the A or U unit intended to take part in a novel glycosylation reaction. These groups are removable in the presence of other groups present on the units of the starting products by recreating an alcohol, which permits in repeating the preceding step of glycosylation elongation of the glucid skeleton.

The invention hence provides access to the synthesis of oligosaccharides with varied enchainments, whether it relates to $\alpha$ or $\beta$ stereo-specificity and/or the order of enchainment between the x, y and z units, lengthening being producible as desired.

According to yet another feature of the process of the invention, the developed glucid chain is subject to one or several chemical reactions in order to introduce a given type of functional group or, successively, several types of groups, then to form, if desired, derivatives of these functional groups.

This functionalisation step may be effected by eliminating only certain protective groups and/or certain precursor groups of the amino derivatives or again the whole of the protective groups and/or of the precursor groups and by introducing in their place a given type of substituent or successively different substituents, then by releasing a portion or all of the —OH groups still blocked, if desired.

It is understood then that the various groups present on the units of the chain are compatible with the substituent introduced at each step.

The one or more chemical reactions applied in the course of the functionalisation steps are carried out so as not to alter the structure of the chain and the groups that it is desired if necessary to maintain and/or those which have already been introduced.

According to a preferred embodiment of the invention, to obtain oligosaccharides with specific substitutions as defined above, starting materials are advantageously used containing several types of protective groups, namely (1) one or several semi-permanent groups and (2) one or several permanent groups.

By semi-permanent groups, is meant groups removable in the first place after the reactions of glycosylation when the glucid skeleton includes the number of desired units, without removal or alteration of the other groups present, then enabling the introduction of the desired functional groups at the positions that they occupy.

The permanent groups are groups capable of maintaining the protection of the —OH radicals during the introduction of the functional groups in place of the semi-permanent groups.

These groups are selected from among those compatible with the functional groups introduced after removal of the semi-permanent groups. It concerns, in addition, groups inert with respect to the reactions carried out for the positioning of these functional groups and which are removable without the functional groups being altered.

Advantageously, the practising of these arrangements enables the development of a glucid chain in which the A and U units are selectively substituted.

To prepare more particularly oligosaccharides containing A and/or U units of the biologically active molecules mentioned above, recourse is advantageously had to protective groups such as acyl, alkyl possibly substituted or aryl radicals.

The units of the products employed of type A comprise, at the 2 position, a nitrogen group permitting the maintenance of the presence of a nitrogen function during the operations applied in the process. This nitrogen group is advantageously constituted by groups such as —$N_3$ or N-phthalimido, or any other group consisting of a precursor of the amine function or of an amine derivative, in particular —NH-acyl, more especially —NH—$COCH_3$ and optionally —$NHSO_3^-$.

As for the carboxyl functions of the U units, they are blocked by groups inert with respect to reactions used for the replacement of the protective groups and removal at the end of the synthesis to liberate the carboxyl groups, possibly for the purposes of salt formation. These protective groups of carboxyl function are selected advantageously from among alkyl radicals or aryl radicals.

The carboxyl functions are also obtainable after glycosylation with a neutral sugar followed by a selective deblocking and an oxydation of the primary alcohol function.

The structure of the product employed in the glycosylation reaction is selected as a function of the units of the glucide skeleton desired as well as of the desired substitutions.

To form, for example, a disaccharide of —U—A— type, two compounds respectively with uronic acid and amino sugar structure, corresponding, in addition to the above-mentioned definitions, are used.

For chain lengthening, these compounds as employed to form the disaccharide concerned, contain, in addition, a temporary group on the position intended to be involved in the new glycosylation reaction. For U—A disaccharide lengthening towards the left, this temporary group is present on the U unit and for lengthening to the right on the A unit.

It is thus possible to obtain, in particular, enchainments $U_w A_x U_y A_z$ in which the sum of the indices is comprised between 2 and 12, these values being included in the range, where w and y cannot be nil simultaneously. Regular enchainments are of the type $U (AU)_n$, $(AU)_n A$, $(UA)_n$ or again $(AU)_n$ with n 1 to 6.

According to a modification of the process of the invention, the alternation of A—U or U—A type encountered in the structures of natural products can be modified by using, in place of the one or several A or U units, a sugar constituting a structural analog of an A or U unit, such as a neutral sugar or a desoxy-sugar, or again other uronic acid units or amino sugars U or A of different configurations.

In a preferred embodiment of the process of the invention, the above alcohol is reacted with a reactive derivative such as a halide, an imidate or an orthoester. These condensations are carried out under anhydrous conditions.

The condensation reaction between the halide and the alcohol is advantageously of the Koenigs-Knorr type. The halide is advantageously constituted by a bromide or a chloride by reason of the ease of production.

Operations are in a solvent medium, more especially in an organic solvent, particularly of the dichloromethane or dichloroethane type.

Advantageously a catalyst is used, generally a silver or mercury salt, for example, silver trifluoromethane sulphonate, commonly called silver triflate, silver carbonate, silver oxide, mercuric bromide or mercuric cyanide. Also a proton acceptor is used such as sym-collidine in the same way as an extractor for the water possibly present and/or for the halohydric acid formed, for example 4 Å molecular sieves.

Study of the reaction conditions show that it is appropriate to operate at room temperature or again at a lower temperature which can reach 0° C. or less, in an atmosphere of an inert gas such as nitrogen or argon.

These conditions enable the units of structure x and y or z (or the reverse), to be condensed, in the desired stereo-chemistry. They also permit the establishment of covalent bonds with neutral sugars or desoxy-sugars.

A modification comprising the use, as catalyst, of mercuric derivatives, in particular of cyanide and/or or mercuric bromide, is established to be suitable for forming covalent bonds between alcohols of various structures and an L-idose precursor of the unit of z structure (L-iduronic acid). According to this modification, 4 Å molecular sieves are also used. The organic solvent is selected according to the reactivity of the alcohol. Thus advantageously there is used a solvent of the type of nitrobenzene when the condensation requires a temperature higher than 100° C. For lower temperatures, solvents such as benzene or dichloromethane are used. Mixtures of solvents are also suitable to carry out the condensation reaction.

With units of type U, it is possible to use, as reagent group an orthoester. The reaction is then preferably carried out at a temperature above 100° C.

The solvent medium is of the chlorobenzene type or any other solvent whose boiling point exceeds 100° C. and it is advantageously between 100° and 150° C. To activate the reaction, a catalyst such as 2,6-dimethyl pyridinium perchlorate is used.

This embodiment of the condensation step is found to be of great interest to form an interglycoside linkage between a unit of U (uronic acid) and a unit of structure A (D-galactosamine).

The use of the orthoester group has in particular a double advantage.

On the one hand, it permits conferring on the anomeric carbon of U the necessary reactivity for the glycosylation reaction. On the other hand, the opening of U group ensures the positioning at the 2 position of of a protective group, selectively removable, thereby permitting the introduction in its place, of a specific substituent group.

Thus, by the reaction of a 1,2-o-methoxy-ethylidene group of a U unit with the —OH radical of an x unit, it is possible at the same time to establish an interglycoside linkage between the two products used and to have at the 2 position of U an —OAc group (Ac representing an acetyl group) which could be removed selectively for the purposes of introduction of a given functional group, for example —$SO_3^-$. This feature also permits full liberty to be left for treating the 4 position of the U unit.

When an imidoyl group is used as the reagent group, it is found to be appropriate to operate at low temperature, more especially at a temperature below or equal to about 0° C., in a solvent medium, such as dichloromethane, in the presence of a 4 Å molecular sieve and a catalyst such as boron trifluoride etherate.

In the starting alcohol, the free —OH group occupies the position that it is desired to engage in the glycosylation linkage.

By selecting the alcohol suitably, it is thus possible to form linkages of the 1-2, 1-3, 1-4 or 1-6 type.

From the sequence formed at the end of the condensation reaction, a chain is developed including the desired number of units by repeating the glycosylation step.

The alcohol function of one of the units A or U involved in the glucide sequence already constituted is then advantageously liberated from its temporary protective group. The choice of this group will be easily determined by the technician skilled in the art according to the nature of the other groups present on the glucide chain.

Among the various groups which can be used, is mentioned the allyl group which, by treatment, for example first with an isomerising agent such as Pd, Rh and Ir derivatives, in particular rhodium tris-triphenylphosphine chloride (I), or again potassium tertio-butoxide, then under acid conditions, in particular with a mixture of mercuric oxide and mercuric chloride, enable the recreation easily of an alcohol at the position that it occupies.

In the same way, it is possible to obtain an —OH group by saponification from an —O-acyl group, in particular —O-acetyl or —O-chloroacetyl or —O-levulinovl.

These radicals can be removed to liberate an —OH function, for example, by means of thiourea in a solvent medium, advantageously at a temperature higher than 80° C., preferably of the order of 100° C.

The foregoing arrangements enable the production of a glucide chain with alternate A—U or U—A units.

This regular alternation can be modified by applying suitable substances in the glycosylation reaction. It is thus possible to develop an irregular structure with the incorporation of units other than U or A, in particular neutral sugars or again desoxy-sugars. Another type of irregular structure can be obtained by adding several consecutive A units or U units between two A—U or U—A structural units.

It is understood that the various arrangements of the invention relating to the A and U units are applied equally to other units which can include the glucide chain, such as neutral sugars or desoxy-sugars.

As has already been indicated, the various groups present on the A and U units are selected so as to confer on the latter sufficient reactivity to produce the glycoside linkage concerned.

The —OH radical protective groups, apart from the temporary groups already considered, are generally selected from the group comprising acyl radicals (particularly acetyl, alkyl, substituted alkyl such as benzyl), and for two neighbouring positions, among the acetal groups or Ketals, for example benzylidene. Another form of protection consists of carrying out blocking of two —OH groups in epoxide form or of 1,6-anhydro bridge.

Advantageously, the products used in the glycosylation reaction contain several types of protective groups, which permits in the course of the step of functionalisation the successive introduction of one or several functional groups and the liberation of one or several —OH radicals if desired.

In general, the protective groups may already occupy certain positions on the products applied in the glycosylation reaction.

They may also be introduced from other groups once the glucide skeleton is constituted. This modification comprises, for example, the use for glycosylation of a substance A in which the —OH groups at the 2 and 3 positions and at the 1 and 6 positions are blocked in anhydrous form, respectively 2,3-epoxide and 1,6-anhydro. Due to this blocking, during the development of the glucide skeleton there is available an element constituting potentially an A unit but not interfering with the reactions applied in the synthesis. This arrangement has the advantage of allowing wide liberty to carry out desired reactions on the groups of the other units.

It will be noted, in addition, in the case concerned, that the opening of the epoxide function by the sodium azide enables the introduction, at the 2 position, of an $N_3$ group which hence constitutes a precursor of an amine function.

Preferably, to have available a glucide chain permitting the introduction successively of one or several types of substituents in the course of the functionalisation step, in particular the specific substitutions above, products are applied comprising several types of protective groups, namely the semi-permanent groups and the permanent groups defined above.

As already indicated, the substitutions of the natural products concerned, apart from those of the 2 positions of the A units, are essentially constituted by sulphate groups.

Applicants researches to perfect the suitable sulphation conditions have shown that it is possible and even advantageous to carry out a sulphation reaction in the presence of benzyl groups. Contrary to opinions accepted in this field, the removal of benzyl permanent groups, in the presence of sulphate groups, can be effected.

Preferably, the —OH radicals of the starting materials intended to be sulphated are then protected by acyl groups, in particular acetyl, whilst the —OH radicals intended to be liberated at the end of the synthesis are protected by a permanent group such as the benzyl group.

By the high flexibility of the process of the invention, it is possible to subject all of the glucide chain formed to a given chemical reaction in order to introduce a particular type of substituent.

This treatment can consist, for example, of esterification, particularly sulphation by means of a suitable agent, carried out under conditions not changing the oside structure. This sulphation can be carried specifically or not, as necessary on the fully protected glycoside.

In a preferred embodiment of the invention, the functionalisation step is however effected selectively so as to introduce on the chain, successively, several types of substituent and then certain —OH radicals to be liberated.

By particularly advantageous conditions, enabling the introduction of the sulphate groups on the predetermined positions of the units, to free the —OH radicals at other positions, to form at the 2 position of the A units an amino derivative and in the 6 position U units of the acid derivatives, units corresponding to the following characteristics are applied.

The semi-permanent groups of these units occupy positions intended to be sulphated and are constituted by —O-acetyl groups.

As for the positions corresponding to an —OH group intended to be liberated, they are occupied by semi-permanent groups constituted by benzyl groups or permanent groups.

The 2 positions of the A units are substituted by groups such as $N_3$, NH-phthalimidoyl or —NH-acetyl and the 6 positions of the U units are occupied by carboxyl groups protected by an alkyl radical, in particular methyl.

This set of conditions enables the realisation of the functionalisation step, for example as follows:

First there is introduced selectively the sulphate groups after having eliminated the —O-acetyl blocking groups. This reaction is carried out so as not to affect the benzyl groups and the nitrogen and carboxyl groups present.

In this respect, advantageously a saponification reaction is carried out by means of a strong base such as soda.

This reaction is carried out preferably at a temperature below ambient temperature and more especially close to 0° C.

The product resulting from the hydrolysis is subjected to the action of an alkylation agent in order to introduce, on the carboxyl group, the protected alkyl groups which are found to be removed on hydrolysis.

By reaction with a sulphation agent, the introduction of sulphate groups at the positions released by hydrolysis and left free after the action of the alkylation agent, is then obtained.

Satisfactory reaction conditions for the sulphation comprise the utilisation of a sulphation agent, such as a trimethylamine/$SO_3^-$ complex. This reaction is advantageously carried out in a solvent medium, more especially in a solvent such as dimethylformamide. Preferably operation is at a temperature higher than room temperature, generally in the vicinity of 50° C., which corresponds to a reaction time of about 12 hours.

After the introduction of the sulphate groups on the alcohol functions, the liberation of the —OH groups blocked by the benzyl radicals follows.

The removal of benzyl groups is advantageously done by catalytic hydrogenation under conditions compatible with the maintenance of the sulphate groups and the conversion of the nitrogenous groups into amino functional groups.

Preferably the operation is carried out under hydrogen pressure in the presence of a catalyst of the Pd/C type.

This reaction is advantageously carried out in an organic solvent medium, in particular alcoholic, supplemented with water.

To obtain hydrogenation of the precursor nitrogenous groups and the removal of the protective radicals from the —OH groups, the reaction is advantageously carried out over a period of about 3 to 4 days.

As already indicated, the amino functional groups are in the form of derivatives of the N-acetyl type in the biologically active molecules concerned.

To form N-acetyl groups, the product resulting from the hydrogenation reaction is subjected to an acetylation agent. In this respect, acetic anhydride constitutes a particularly suitable agent.

To carry out this selective acetylation reaction without affecting the other substituents present on the units, it is appropriate, in particular, to operate at a basic pH, in particular close to 8 in an aqueous medium.

It may also be desired to form N-sulphate groups which may be done by means of a sulphation agent of the above-indicated type. pHs higher than 9, advantageously of the order to 9-10, are used for the sulphation.

After the sulphation or acetylation reaction, the addition of a strong base enables the liberation of the carboxyl groups.

The products formed may easily be salted by exchange resins with an appropriate cation. In natural products, the cation in particular is constituted by sodium. Hence exchange resins with sodium cations are advantageously used.

It is also possible to form salts of potassium, lithium, magnesium, calcium. A proton exchange resin is then used, and then the acid formed is neutralised with the base of the cation.

The invention is also directed to oligosaccharides constituting intermediates in the various steps of the process of synthesis defined above.

In one family, these oligosaccharides include at least one binary A—U and U—A unit completely protected and possessing either a reactive group on the anomeric carbon of the unit at the reducing end, or a single free —OH group on the unit at the non-reducing end, this —OH group occupying the 3, 4 or 6 position in the case of an A unit and the 2, 3 or 4 positions in the case of U units.

In another family, the oligosaccharides are constituted by completely protected units such as obtained at the end of the glycosylation step. Another family again comprises products in which one or several —OH groups are liberated.

These various oligosaccharides comprise a chain based on binary units of structure $(A-U)_n$ or $(U-A)_n$ in which n is a number from 1 to 6.

These oligosaccharides correspond to an enchainment of the type x-y or x-z.

In one group of intermediate oligosaccharides of the invention, the glycoside chain is constituted by a single type of these binary enchainments.

In another group, several of these types are present. Corresponding oligosaccharides include in their chains x-y and x-z.

It is understood that the order of the enchainments concerned above in one or several of the binary units, can be reversed according to the invention.

According to one modification, the intermediate oligosaccharides defined above contain one or several consecutive x or again y or z units.

According to another modification, the intermediate oligosaccharides contain one or several units of neutral sugars and/or several desoxy-sugars in their structure. The various protective groups of these sugars corespond to the definitions given above or the A and U units.

In these oligosaccharides, the constituent units are connected to one another by linkages of 1-2, 1-3, 1-4, or 1-6 type according to the nature the alcohol utilised in the glycosylation step.

The oligosaccharides having the structure of fragments of chondroitins, chondroitin-sulphates or dermatane-sulphate contain linkages of the $$1 \xrightarrow{\beta} 3$$

type and comprise respectively $$y\ 1 \xrightarrow{\beta} 3\ x,\ z\ 1 \xrightarrow{\alpha} x,\ x\ 1 \xrightarrow{\beta} 4\ z\ \text{and}\ x\ 1 \xrightarrow{\beta} 4\ y.$$

One group of preferred oligosaccharides contains at least one binary unit possessing a structure of the type x $$1 \xrightarrow{\beta} 4y,$$

that is to say [D-galactosamine]

$$1 \xrightarrow{\beta} 4$$

[D-glucuronic acid] corresponding to formula I:

in which:
the $R_1$ radicals, identical or different from one another, if necessary conjointly with R, represent a protective group, in particular a sp semi-permanent group or a p permanent group, T, a temporary group t, or a permanent group p, or a hydrogen atom, N, is a nitrogenous group amine or amine derivative precursor.

R, an aliphatic or aromatic radical, particularly an alkyl radical comprising from 1 to 4 carbon atoms, where OR represents a reactive group such as a halide or again R an alkyl radical and M, a group blocking the acid function, these various symbols having the above-given meanings.

In a sub-group, all the radicals R, $R_1$ and T are identical and represent a p or sp group.

In another sub-group, the radicals $R_1$ are different from one another, one at least representing a sp type group, possibly conjointly with R, the one or more other radicals $R_1$ representing a p group.

It will be noted that the general meanings of the symbols of formula I are applied also to the formulae of the various groups considered below. In the same way, there is to be found again in each of these groups, particularly, the two sub-groups mentioned above.

Preferred oligosaccharides correspond to the following formulae (II) to (V):

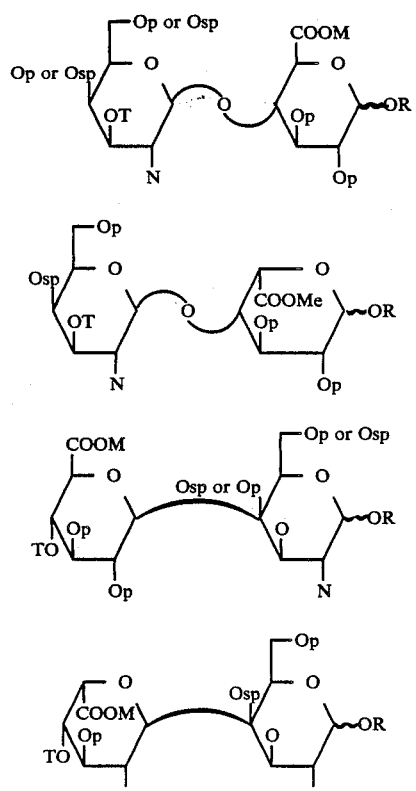

It will be noted that the oligosaccharides (II) and (IV) enable esterification reactions, particularly sulfatation reactions, to be carried out on the 4 and/or 6 positions of the galactosamine and glucuronic acid respectively whilst the chain can be elongated.

With those of formulae (III) and (V), it is possible to carry out said reactions on the 4 positions of the galactosamine or the iduronic acid respectively, while the chain can be elongated if desired.

Preferably, in the formulae (II) to (V), the symbols given have independently, or in combination, the following meanings:

M represents a hydrogen atom or an alkyl radical, particularly methyl, sp an acyl group, in particular acetyl, p, a substituted alkyl group, in particular benzyl, R, an acyl group at $\alpha$ or $\beta$, in particular an acetyl group, an alkyl radical, in particular methyl or substituted alkyl, particularly benzyl, or —OR a halogen, in particular a bromide, or again an imidoyl radical, N, an azido or a phthalimido group, T, the group t representing an acyl radical, in particular acetyl, a halogenated acyl radical, in particular, a monochloro or trichloroacetyl radical, or the group p representing a substituted alkyl radical in particular the benzyl radical, as the case may be itself paramethoxy or again a hydrogen atom.

Another preferred family of intermediate oligosaccharides entering into the scope of the invention corresponds to the products from which the protective groups have been partially removed in the course of synthesis. In particular, such products include an —OH group in place of the sp groups.

A preferred group of intermediate trisaccharides has a structure corresponding to one of the formulae (VI) to (IX).

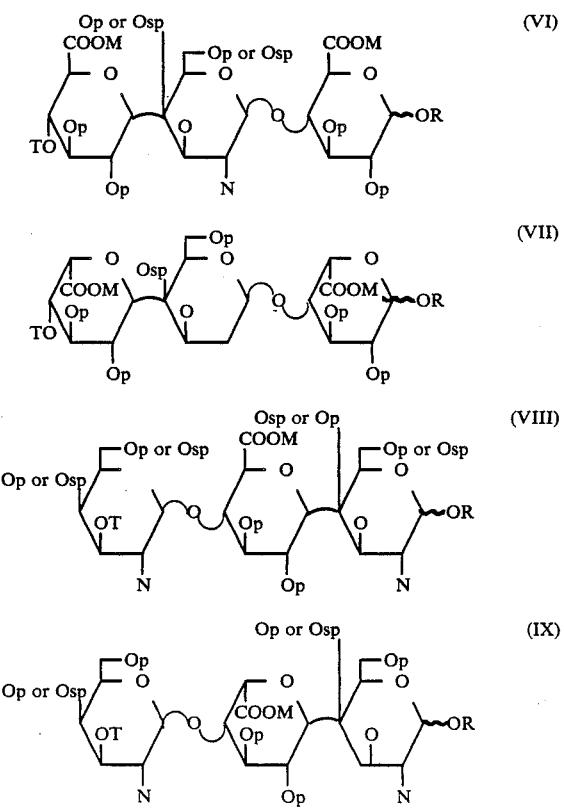

in which the various symbols have the above-given meanings.

Other preferred intermediate oligosaccharides are constituted by tetrasaccharides. A more especially advantageous tetrasaccharide possesses the structure (X):

As mentioned above for binary units, the invention relates also to the above oligosaccharides in which one, several or, as the case may be, all of the —OH groups are liberated in the course of synthesis.

The invention is aimed, in addition, as novel products, at the oligosaccharides corresponding respectively to the various definitions given above, but including one or several functional groups.

These functional groups are constituted preferably, by esters, and occur more especially in the form of inorganic anions.

Particularly preferred esters, by reason of their presence in biologically active molecules of the type of chondroitins and chondroitin-sulphates and dermatane-sulphate are constituted by sulphate esters.

Other advantageous esters correspond to phosphate esters.

These functional groups are borne by one or several primary alcohols and/or secondary alcohol and/or primary amine functions.

A preferred family of oligosaccharides of the invention thus includes x unit comprising such an anion as defined above at the 6 and/or 4 position.

Oligosaccharides of this family contain, at the 2 position of x a primary amine functional group advantageously substituted by a sulphate or by another substituent group.

In the oligosaccharides of the invention containing at least two units x, the amine functional groups at the 2 position may be substituted by the same group or by different groups.

A preferred group of oligosaccharides of the family concerned includes units x comprising sulphate groups on the secondary alcohol and or the primary alcohol function.

Preferred oligosaccharides of this group comprise at the 2 position of these units a —NH-acyl group, in particular —NH-acetyl, other oligosaccharides comprise a —NHSO$_3^-$ group.

Preferably, the esters below occur in the form of salt with an inorganic or organic cation, in particular a metal cation, particularly an alkali cation, or again a cation derived from a nitrogenous organic base, for example triethylammonium.

The cations used are constituted by sodium. Other cations are suitable such as the potassium, magnesium or calcium cations.

In another preferred family of oligosaccharides of the invention, the carboxyl groups of units y or z are free or are preferably in the form of salt with an organic or inorganic cation such as defined above. They may also be protected as reported above.

Other preferred products have sulphates on the y unit.

In these various families of oligosaccharides, the hydroxyl functions of the pyran rings and more particularly the anomeric hydroxyl (for stability reasons) are either free, or protected by permanent groups of the alkyl type, in particular by methyl groups.

Preferred products of these various families contain, in combination, the units A and U corresponding to the above characteristics.

Pharmacological study of the oligosaccharides of this structural type has shown in certain of these compounds biological activities enabling them to control specifically certain steps in blood coagulation (see Griffith M. J. et al. Biochem. Biophys. Res. Commun., 112 (1983) 663–670).

The invention therefore relates also to their use in the constitution of biological reagents, useful in laboratory, particularly as comparison elements for the study of other substances of which it is desired to test the activity on coagulation.

The works of the applicant have shown that this type of product is capable of exerting a powerful anti-thrombotic activity (E. G. Vairel et al. Ann. Pharm. Franc. in press). In addition, derivatives according to the invention have great interest for combating disorders of the vascular wall, (atheroscleroses and arterioscleroses) and aging of the tissues. They also exhibit an action with respect to the cellular adhesion.

In addition, they have the advantage of not having the effect of activation on platelet aggregation and not resulting in thrombocytopenia. They have also the advantage of being practically devoid of effect on bleeding time, which eliminates the risks of hemorrhage. These two properties are extremely important for medical uses.

The oligosaccharides of the invention are, in addition, advantageously devoid of toxicity.

These products are hence particularly valuable for developing medicaments useful, particularly for the treatment of coagulation disorders, aging of tissues and disorders of cellular proliferation.

The invention hence relates also to pharmaceutical preparations which contain said oligosaccharides.

It relates more particularly to pharmaceutical preparations devoid of pyrogenic substances containing an effective amount of active principles in association with pharmaceutical excipients.

It also relates to the compositions in which the pharmaceutical vehicle is suited for administration orally. Suitable administrative forms of the invention for oral administration may advantageously be gastroresistant capsules, pellets or tablets, pills, or again presented in liposome form or of drinkable solutions. Said preparations contain advantageously from 50 mg to 5 g by weight unit, preferably 100 to 250 mg for tablets and pills and 1 to 5 g for drinkable solutions.

Other pharmaceutical compositions comprise these oligosaccharides in association with suitable excipients for rectal administration. Corresponding administrative forms are constituted by suppositories.

Other administrative forms of the invention are constituted by aerosols or pommades.

The invention relates also to sterile or sterilizable injectable pharmaceutical compositions for administration both intravenously and intramuscularly or subcutaneously.

These solutions contain advantageously 50 to 250 mg of oligosaccharides, preferably from 100 to 150, for example of 150 mg/ml, when these solutions are intended for subcutaneous injection. They may contain for example from 25 to 250 particularly 150 mg/ml of oligosaccharides when they are intended for injection intravenously or by perfusion.

Advantageously, such pharmaceutical preparations are presented in the form of ready-for-use discardable syringes. Other preparations are presented in the form of drinkable solutions containing advantageously 500 mg to 5 g of active principle.

The invention relates also to the pharmaceutical compositions containing said oligosaccharides in association with another active principle, useful in particular for prophylaxis and treatment of thrombosis, such as a veinotonic agent like dihydroergotamine, nicotinic acid salt or a thrombolytic agent like urokinase.

The pharmaceutical compositions of the invention are particularly adapted for the control (preventive or curative) of certain stages of blood coagulation in man or in the animal, particularly in the case where the patient is subject to risks of hypercoagulability resulting particularly from surgical operations, from atheromatous processes, from the development of tumors and disorders of blood clotting by bacterial or enzymatic activators.

The compositions of the invention are particularly suited to combat aging of the tissues or manifestations of the degenerative type such as alopecias.

They are useful also for treating atherosclerosis and cellular proliferation disorders.

In order to illustrate the invention, there is indicated, below, an example of the posology usable in man: this posology comprises, for example, the administration to the patient of 50 mg to 150 g subcutaneously, once to thrice daily, according to the level of the risks of hypercoagulability or the thrombotic condition of the patient, or of 150 mg/24 hours, intravenously, in discontinuous administration at regular intervals, or continuous by perfusion, or again from 150 mg (three times weekly) intramuscularly or subcutaneously (these titers being expressed in Yin-Xessler units). These doses can naturally be adjusted for each patient according to results and blood analyses carried out previously, the nature of the disorders from which he suffers and, generally, his state of health.

Besides the pharmaceutical compositions containing the oligosaccharides as such, the invention is aimed also at pharmaceutical compositions containing at least one oligosaccharide as defined above, conjugated, by a covalent bond, to a soluble support or an insoluble support, advantageously by means of the reducing terminal sugar.

Other preferred conjugates with soluble supports are formed from an oligosaccharide fixed to a vehicle such as a protein, particularly polylysine, or bovin albumin serum.

These products are useful as immunogens themselves sources of circulating antibodies produced in vivo or of monoclonal antibodies cloned in vitro by suitable techniques.

In other preferred conjugates the oligosaccharides of the invetion are conjugated to insoluble supports. Advantageously conventional supports are utilized.

These conjugates are useful as immuncabsorbents, for example for its estimation or for the development by fixing to biocompatible polymers, of novel athrombotic hemocompatible polymers.

The invention is directed also to the use of the oligosaccharides concerned in nuclear medicine, as radiopharmaceutical products. These products are then labelled by tracers selected from among those currently used in this field, and particularly by means of technetium 99 m.

To this end, the technetium 99 m obtained from commercial generators is converted, in the form of sodium pertechnetate of unreactive valency 7, into technetium reduced to valency 4 which would be the most reactive form of technetium. This conversion is carried out by means of a reducing system produced from certain tin salts (stannous chloride), iron salts (ferrous sulfate), and titanium salts (titanium trichloride) or other salts.

Most of the time, this simple reduction of the technetium suffices, under given pH conditions, to effect the fixing of the technetium to the molecule concerned.

For the development of these radiopharmaceutical reagents, it is possible to operate in accordance with the method of the P. V. Kulkarni et al. in The Journal of Nuclear Medecine 21, No. 2, p. 117–121.

The so-marked products are advantageously used in in vivo tests for the detection and extended diagnosis of thromboses and of thrombotic states.

The oligosaccharides of the invention may also be used for the determination of the specificity of numerous enzymes involved in the metabolisme of the glycosamino glycans.

Due to their structure, the products of the invention constitute also intermediates of synthesis of great interest enabling the obtaining of given fragments, or of derivatives of fragments, of biologically active molecules. They constitute, particularly, reference compounds for structure studies.

Other advantageous characteristics of the invention will appear from the examples which follow and with reference to FIGS. 1 to 12 illustrating the products employed in the syntheses described.

In these FIGS. 1 to 12, the numerical references of the formulae are used also in the Examples to denote the same products.

The abreviations used in these formulae have the following meanings: Ac: an acetyl group; Me: methyl; Bn: benzyl; Bz: benzoyl; MCAO: monochloroacetyl; Tr: trityl; but.: butyl; S and SO$_3^-$ group; Pht: phthalimidoyl and L: levulinoyl group.

EXAMPLE 1

Figure 2:
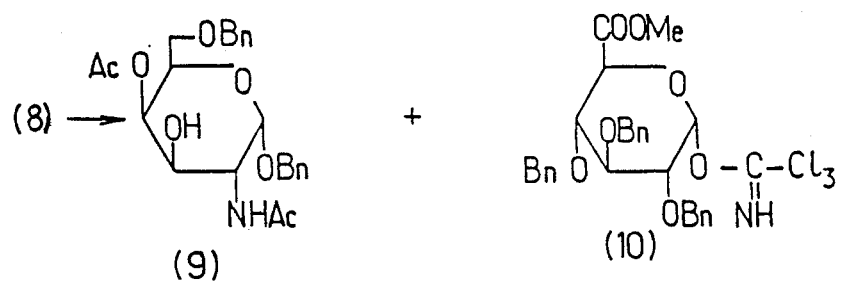
Figure 2:
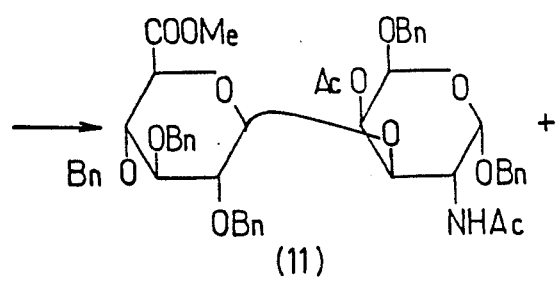
Figure 2:
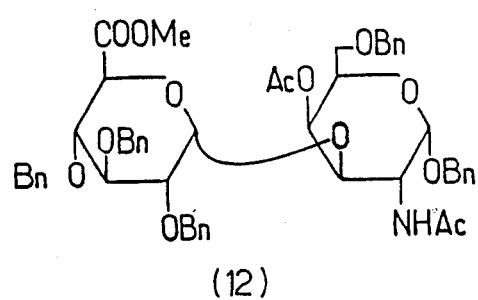
Figure 3:
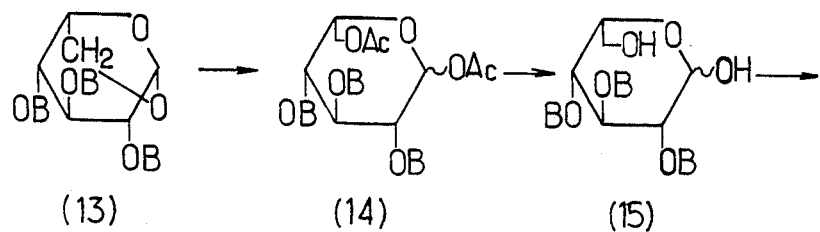
Figure 3:
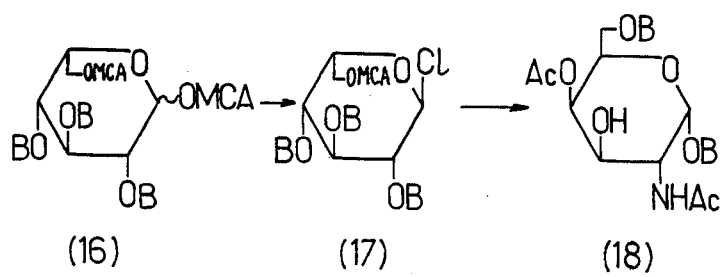
Figure 3:
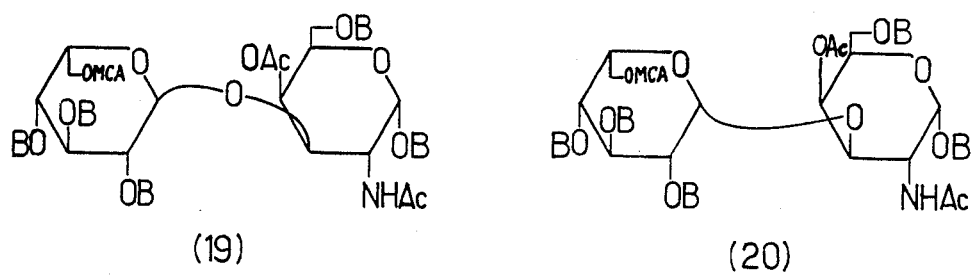
Figure 3:
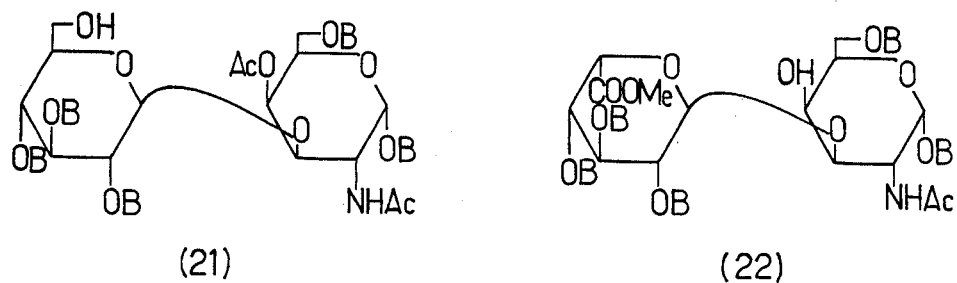
Figure 4:
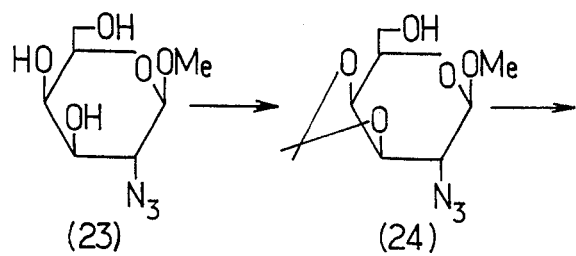
Figure 4:
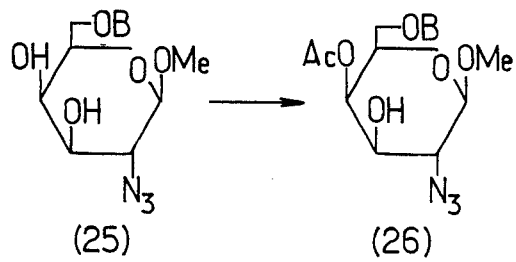
Figure 5:
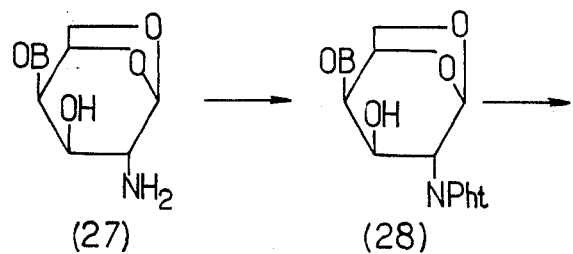
Figure 5:
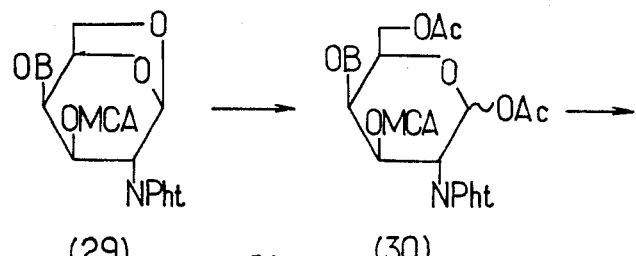
Figure 5:
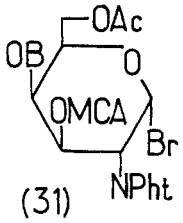

Synthesis of disaccharides 11 and 12 of formulae (see FIGS. 1 and 2)

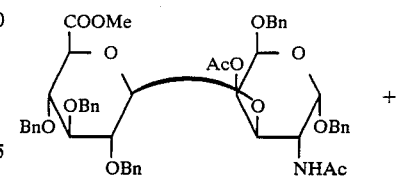

11

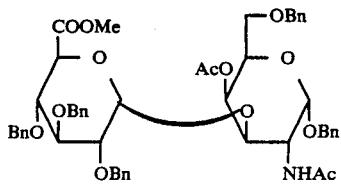

12

(1) Preparation of benzyl-2-acetamido-2-desoxy-α-D-galactopyranoside 2

A suspension of N-acetyl-D-galactosamine 1 (3 g) in anhydrous benzyl alcohol (40 ml) containing 2% hydrochloric acid (gas, dried) is stirred at 70° C. protected from moisture for 16 hours. After cooling, the clear solution is poured slowly into cold ether (400 ml). The precipitate is then cooled 2 hours at −20° C., then drained. The solids are rinsed with ether, then dissolved in a methanol-water mixture (4:1, v/v, 100 ml) and brought to boiling for ½ hour in the presence of active charcoal (1 g). The hot solution is filtered, then evaporated to dryness. The residue is subjected to fractional crystallisation in 2-propanol to give the compound 2 (2.54 g, 60%)

M.P. = 205°–206° C.;

$[\alpha]_D$ +210° (c 7, $H_2O$).

(Lit.: H. M. Flowers and D. Shapiro), *J. Org. Chem.*, 30 (1965) 2041–43,

M.P. = 203°–205°, $[\alpha]_D$ +204° (c 0.98, $H_2O$)).

(2) Acetalation of the compound 2

(a) Acetalation by acetone in an acid medium.

A suspension of the compound 2 (311 mg, 1 mM) in anhydrous acetone (20 ml) is stirred protected from moisture in the presence of para-toluenesulfonic acid (monohydrate 40 mg). The mixture becomes homogeneous after 1 hour, and is stirred 3 hours 30 in total. Triethylamine (0.5 l) is added and the reaction mixture is evaporated to dryness. The residue is taken up again with chloroform (50 ml), the organic phase is washed with 5% aqueous solution of sodium hydrogen carbonate, with water, dried (sodium sulfate), filtered and evaporated. The residue is chromatographed on a silica gel column (20 g). Elution by ethyl acetate gives:

the compound 3, syrup, (222 mg, 63%), $[\alpha]_D$ +193° (cl, methanol), N.M.R. (9C $MH_z$, $CDCl_3$):δ:7.3L (s, 5H, Ph); 5.95 (d, 1H, NH, J=8.5 $H_z$), 4.92 (d, 1H, 1.97 $H_1$, $J_{1,2}$=3.5 $H_z$), 2.80 (1H, OH, exchanged with $D_2O$), 1.97 (s, 3H, NAc), 1.55 and 1.32 (2s, 2×3H, Isopropyl):

the compound 4, syrup (110 mg, 31%); $[\alpha]_D$ +154° (cl, chloroform), N.M.R. (90 $MH_z$, $CDCl_3$):δ:5.32 (s, 5H, Ph), 5.80 (d, 1H, NH, J=8.5 $H_z$), 5.0 (d, 1H, $H_1$ $J_{1,2}$=3.5 $H_z$); 2.75 (1H, OH, exchanged with $D_2O$); 1.95 (s, 3H, NAc); 1.46 (s, 6H, Isopropyl).

(b) Acetelation with 2-methoxypropene (kinetic check)

The compound 2 (311 mg, 1 mM) is dissolved in anhydrous N,N-dimethylformamide (8 ml). 2-methoxypropene (0.3 ml) and para-toluenesulfonic acid (monohydrate 3 mg) are added successively, and the reaction mixture is stirred protected from moisture for 3 hours.

An identical treatment with that described in paragraph a, followed by chromatography on a silica gel column (20 g) gives, by elution with the dichloromethane-methanol mixture (15:1, v/v, containing 0.1% of triethylamine). the compound 3, syrup (34 mg, 10%) the compound 4, syrup (299 mg, 85%)

Benzoylation of the compound 4

A solution of the compound 4 (90 mg, 0.25 mM) in a mixture of anhydrous dichloromethane (5 ml) and anhydrous pyridine (1 ml) is treated at 0° C. protected from moisture with benzoyl chloride (60 μl, 0.5 mM) for four hours. Methanol (1 ml) is then added, and after 15 minutes, the reaction mixture is diluted with dichloromethane (20 ml). The organic phase is washed with a 10% aqueous solution of sodium hydrogensulfate, with water, with a 5% aqueous solution of sodium hydrogensulfate with water, dried (sodium sulfate), filtered and evaporated. The gelatinous residue is crystallized in a ethyl acetate-ether-hexane mixture to give the compound 5 (105 mg, 90%), PF=185°–186° C.; $[\alpha]_D$ +198° H ortho benzoyl); 7.40 (, 8H, 1Ph+H meta, para benzoyl), 5.73 (d, 1H, NH, J=9$H_z$), 5.33 (d. of d., 1H, $H_3$, $J_{2,3}$=10$H_z$, $J_{3,4}$=3.5 $H_z$), 1.83 (s, 3H, NAc), 1.48 and 1.39 (2s, ×3H, Isopropyl).

N.B.: The presence at δ=5.33 ppm of a doublet of a doublet having coupling constants of 10 and 35 $H_z$ shows unambiguously the presence of an electroattracting group (benzoate) at C-3, and hence ensures the position at 4 and 6 of isopropylydene.

Selective hydrolysis and benzoylation at the 6 position of the compound 5

A mixture of the compound 5 (72 mg) and 80% acetic acid (5 ml) is heated to 100° C. with stirring for 30 minutes. After cooling to room temperature, the reaction mixture is evaporated to dryness, evaporated with water (3 times 10 ml), then with toluene. The solid residue is dried in a dessicater under high vacuum.

The crude diol is dissolved in a mixture of anhydrous pyridine (0.5 ml) and dichloromethane (3 ml). Benzoyl cyanide (33 mg) is added and the reaction mixture is stirred for 16 hours. Methanol (5 ml) is added and, after 1 hour with stirring, the reaction mixture is evaporated to dryness. The residue is crystallized in a mixture of ethyl acetate-hexane to give the compound 6 (71 mg, 86% from compound 154); MP=180°–181° C.; $[\alpha]_D$ +109° (cl, chloroform); N.M.R. (90 $MH_z$, $CDCl_3$):δ:8.02 (m, 4H, H ortho 2-benzoyl); 5.88 (d, 1H, NH, J=9$H_z$); 5.38 (d, of d., 1H, H 3, $J_{2,3}$=10$H_z$, $J_{3,4}$=3$H_z$), 5.02 (d, 1H, $H_1$, $J_{1,2}$=35$H_z$), 3.30 (1H, OH, exchanged with $D_2O$, 1.81 (s, 3H, NAc).

It will be noted that by benzylation, O-debenzoylation, then selective acylation at the C-6 position, the compound can result in a derivative of the type

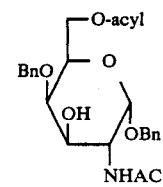

which is a suitably protected precursor useful for the synthesis of chondroitin-6-sulfate.

Benzylation of the derivative 3

The compound 2 (200 mg, 057 mM) is dissolved in anhydrous N,N-dimethylformamide (5 ml). Anhydro barytes (700 mg, 4.5 mM), barium hydroxide octahydrate (158 mg, 0.5 mM) and benzyl bromide (120 1, 1 mM) are added successively. The reaction mixture is stirred protected from moisture for 20 hours. Methanol (0.5 ml) is added, then after 30 minutes, the reaction mixture is filtered, the solids are rinsed with chloroform (50 ml). The organic phase is washed with a cold 50% acetic acid solution, with water, with a 5% aqueous solution of sodium hydrogencarbonate, with water, dried (sodium sulfate), filtered and evaporated. The residue is washed on a column of silica gel (10 g). Elution by the mixture ethyl acetate-hexane (3:1, v/v) gives the compound 7 in the form of a colorless glass which it has not been possible to crystallize (228 mg, 91%; $[\alpha]_D$ +136° (c 1.5, chloroform), N.M.R. (90 MH$_z$, CDCl$_3$):$\delta$:7.30 (m, 10H, 2 Ph), 5.86 (d, 1H, NH, J=8.5 H$_z$), 4.89 (d, 1H, H$_1$, J$_{1,2}$=3.5 H$_z$); 1.93 (s, 3H, NAC), 1.55 and 1.31 (2s, 2×3 H; Isopropyl).

Acid hydrolysis of the derivative 7

A mixture of the compound 7 (150 mg) and of 80% acetic acid (5 ml) is stirred at 100° C. for ½ hour. After cooling to room temperature, the reaction mixture is evaporated to dryness, evaporated with water (3 times 10 ml), then with toluene. The gelatinous residue is crystallized in ethanol to give the diol 8 (121 mg, 89%), MP=183°-184° C. $[\alpha]_D$ +171° (cl, methanol).

Preparation of the derivative 4-O-acetylated 9

A mixture of the compound 8 (100 mg), of anhydrous toluene (5 ml), of trimethylorthoacetate (0.5 ml) and para-toluene sulfonic acid (monohydrate, 1 mg) is stirred protected from moisture for 1 hour (the medium becomes homogenous after about 45 minutes). Triethylamine (0.2 ml) is added and the reaction mixture is diluted with toluene (20 ml). The organic phase is washed with water (twice), dried (sodium sulfate), filtered and evaporated. The N.M.R. spectrum of the crude product is in agreement with the expected structure ($\delta$:3.24 (s, 3H, OMe); 1.65 (s, 3H, CME), but the unstable orthoester is used immediately in the following reaction:

A mixture of the preceding orthoester and of 80% acetic acid (5 ml) is stirred 10 minutes at room temperature, then evaporated to dryness. This residue is evaporated with water, then with toluene. Crystallization in an ethyl acetate-hexane mixture gives the compound 9 (95 mg, 85% from compound 8) MP=146°-147° C., $[\alpha]_D$ +94°, (cl, chloroform), N.M.R. (90 NH$_z$, CDCl$_3$):$\delta$:7.32 (m, 10H, 2 Ph), 5.92 (d, 1H, NH, J=8.5 H$_z$), 5.37 (d. of d., 1 H, H$_4$, J$_{3,4}$=8 H$_z$, J$_{4,5}$=1 H$_z$), 4.96 (d, 1H, H 1, J$_{1,2}$=3.5 H$_z$), 3.60 (1H, OH, exchanged with D$_2$O), 2.11 and 1.95 (2s, 2×3 H, OAc and NAc).

(The presence at $\delta$=5.37 of a doublet of a doublet having coupling constants of 3 and 1H$_z$ shows unambiguously the presence of an acylated group (acetate) at C-4).

The derivative 9 is a precurser of choice for the preparation of the basic disaccharide of: chondroitin-4-sulphate, (acid L-iduronic

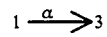

N—Ac—D-galactosamine-4-sulphate).

Condensation between the alcohol 9 and the imidate 10 Imidate 10: Lit.: R. R. Schmidt and G. Grundler, *Synthesis*, (1981) 885-87.

A solution of the alcohol 9 (76 mg, 0.17 mM) and of the imidate 10 (175 mg, 0.28 mM) in anhydrous dichloromethane (2.5 ml) is stirred protected from moisture in the presence of 4 Å molecular sieve (powder, 100 mg). The reaction mixture is cooled to 0° C., and the etherate of boron trifluoride (BF$_3$:Et$_2$ 20, 4 ($\mu$l, 32 $\mu$M) is added all at once. After stirring 1 hour at 0° C., then 3 days at room temperature, sodium hydrogencarbonate (100 mg) is added. After 15 minutes, the solids are drained, rinsed with dichloroethane (50 ml) and the organic phase is washed with a 5% aqueous solution of sodium hydrogencarbonate, with water, dried (sodium sulphate), filtered and evaporated.

The residue is chromatographed on a silica gel column (18 g). Elution by the mixture ethyl acetate-hexane (1:1, v/v) enables the isolation of:

a disaccharide fraction (62 mg), the unreacted starting material (47 mg, 60%).

The disaccharide fraction is rechromatographed on a silica gel column (5 g, gel 230-400 mesh). Elution with the mixture dichloromethane-ethyl acetate (5:1, v/v) enables the isolation of (in order of elution):

the disaccharide

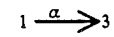

12, colorless syrup (24 mg, 15%), $[\alpha]_D$ +98° (cl, chloroform); N.M.R. (90 MH$_z$, CDCl$_3$):$\delta$:7.30 (m, 25H, 5 Ph); 5.65 (d, 1H, NH, J=9.5 H$_z$); 5.52 (d, of d., 1 H, H$_4$, J$_{3,4}$=3H$_z$); 5.05 (d, 1H, H'$_1$, J$_{1',2'}$=3.5 H$_z$); 4.95 (d, 1H, H1, J$_{1,2}$=3.5 H$_z$); 3.63 (s, 3H, COOMe), 1.92 and 1.82 (2s, 2×3 H, OAc and NAc);

the disaccharide

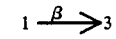

11 colorless syrup (24 mg, 15%), $[\alpha]_D$ +80° (cl, chloroform); N.M.R. (90 MH$_z$, CDCl$_3$):$\delta$:7.30 (m, 25 H, 5 Ph); 5.48 (d, 1H, NH, J=9H$_z$); 5.46 (d. of d., 1H, H$_4$, J$_{3,4}$=3H$_z$); 4.97 (d, 1H, H1, J$_{1,2}$=3.5 H$_z$); 3.78 (s, 3H, COOMe); 2.04 and 1.61 (2s, 2×3H, OAc and NAc.

EXAMPLE 2

Synthesis of a disaccharide having the following structure

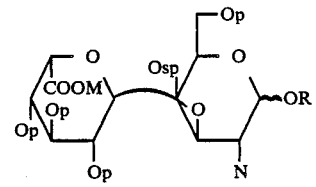

The disaccharide 22 obtained by a synthesis route has the above formula with M being Me, p and R a benzyl group; sp a —OH group and N a NH-acetyl group.

This synthesis is carried out from 1.6- —L— idopyranose according to the following steps 1 to 6: (see FIG. 3)

(1) preparation of 1,6-anhydro-2,3,4-tri-O-benzyl-α-L-idopyranose

To a solution of 1,6-anhydro-α-L-idopyranose (1 g) in anhydrous DMF (60 ml), were added 1.5 g of NaH (50% emulsion in oil) and then 4 ml of benzyl bromide.

After one hour stirring at room temperature, 5 ml of methanol was added and the mixture was concentrated to dryness. The product was extracted with dichloromethane.

The organic phase is washed with water and dried again over sodium sulfate.

The syrup obtained was passed over a silica gel column eluted first with hexane then with a hexane-ethyl acetate mixture (8/1, v/v, then 4/1, v/v). The syrup obtained crystallized in the course of drying (2.5 g - 88%).

The product was recrystallized in an ether-hexane mixture $[\alpha]_{20}^{D} = +30°$ (c=1 chloroform) - MP: 69°-70° C.

(2) acetolysis

A solution of 13 (405 mg) in a mixture of 10 ml of acetic anhydride and 2 ml of fluoroacetic acid were subjected to stirring for 4 hours at room temperature and protected from moisture.

20 ml of xylene was added and then the reaction mixture was evaporated to dryness, the co-evaporation was carried out with xylene (2 times 5 ml) and drying under vacuum was done. 455 mg of compound 14 was obtained (yield 91%), in the form of a colorless syrup. The NMR spectrum agreed with the expected structure. $[\alpha]_D^{20°\ C.} = +2.9°$ (c=1, CHCl$_3$).

(3) removal of the acetyl groups from the compound 14

A solution of the compound 14 (534 mg) was treated in 10 ml of anhydrous methanol at 4° C. with a solution of 0.1 ml of M sodium methylate for about 14 hours.

The reaction mixture was neutralized with amberlite resin IR 120(H+), the resin was filtered and then the solvent was evaporated.

The residue was crystallized in an ether-hexane mixture which resulted in 412 mg of the compound 15 (yield 91%)

MP: 81°-82° C.; $[\alpha]_D^{20°\ C.} = +11°$ (c=1, CHCl$_3$).

NMR spectrum and centesimal analysis agreed with the expected structure.

(3) Monochloroacetylation of the compound 15

A solution of 740 mg of the diol 15 in a mixture of 8 ml of anhydrous dichloromethane and 1 ml of anhydrous pyridine was cooled with stirring to −20° C. under a dry argon atmosphere.

Drop by drop in 10 minutes a solution of 0.40 ml of monochloroacetyl chloride in 2 ml of anhydrous dichloromethane was added.

The mixture was subjected to stirring 40 minutes at −20° C. then poured still with stirring into a water-ice mixture (100 ml).

After one hour, the mixture was extracted with dichloromethane (3 times 20 ml) the organic phases are washed with 10% KH SO$_4$, with water, with saturated NaHCO$_3$, with water then dried over sodium sulfate, filtered and evaporated.

The residue was washed on a silica gel column of 20 g. Elution was carried out by means of a hexane-ethyl acetate mixture (7:2, v/v).

854 mg of compound 16 in the form of a colorless syrup was obtained (yield 87%) $[\alpha]_D^{20°\ C.} = +5°$ (c=1 CHCl$_3$). The NMR spectrum agreed with the expected structure.

(5) preparation of the idopyranosyl chloride 17

A solution of 260 mg of compound 16 in 2 ml of anhydrous dichloromethane was treated at 0° C. with a saturated solution of HCl (dry gas) in 10 ml of anhydrous dichloromethane for 3 hours.

The reaction mixture was then evaporated to dryness, co-evaporated with toluene (3 times 20 ml) and dried under high vacuum. 216 mg of compound 17 were obtained in the form of an unstable colorless syrup (yield 92%). $[\alpha]_D^{20°\ C.} = -41°$ (c=1, CHCl$_3$). The NMR spectrum confirmed the expected structure.

(6) condensation with the chloride 17 and the alcohol 18

A mixture of 153 ml of chloride 17 (0.28 mml) and 80 mg of alcohol 18 (0.18 mmole) in 3.5 ml of anhydrous dichloromethane was subjected to stirring in the presence of 100 mg of 4 Å molecular sieve at room temperature under a dry argon atmosphere.

The mixture was cooled again to −20° C. and then 66 microliters of sym-collidine and 108 mg of silver triflate were added.

The reaction mixture was subjected to stirring protected from light and the temperature was allowed to rise again slowly to ambiant temperature over about 14 hours.

Then the mixture was diluted with 50 ml of dichloromethane and filtered on a celite 545 bed.

The filter was washed with iced 0.1N HCl, with water, saturated in NaHCO$_3$ and then with water.

The filtrate was then dried over sodium sulfate filtered then evaporated.

The residue was chromatographed on a column of 30 gr of silica gel.

Elution by the mixture ethyl acetate-hexane (1:1, v/v) gave in order of elution the disaccharide 19 and the disaccharide 20.

The disaccharide 19 crystallized in an ether-hexane mixture, 45 mg of the product were recovered, which corresponds to a yield of 26%. $[\alpha]_D^{20°\ C.} = +48°$ (c=1 CHCl$_3$). The NMR spectrum confirmed the expected structure.

The disaccharide 20 is in the form of a syrup (117 mg 68%). $[\alpha]_D^{20°\ C.} = +92°$ (c=1 CHCl$_3$). The anomery of the two disaccharides was deduced from the NMR spectra ($J_{1',2'}$0.5 Hz for and $J_{1',2'}=2$ Hz for and from the value of the rotatory power. MP=73°-74° C.

(7) Removal of the monochloroacetyl group at the 6' position

A solution of 19 and 20 (40 mg) in a mixture of pyridine (1 ml) and ethanol (0.2 ml) is shaken for 20 minutes at 100° C. in the presence of thiourea (7 mg). After cooling and the usual treatment, the residue is washed on a silica gel column (2 g). Elution with the mixture hexane-AcOEt (3:1 v/v) gives the compound 21 (30 mg, 81%), colorless syrup.

The NMR spectrum is in accordance with the expected structure.

(8) Oxidation for the passage to idose-iduronic acid

The compound 21 (30 mg) is oxidized at 0° C. in acetone (3 ml) with the mixture CrO$_3$/H$_2$SO$_4$ 3.5M for 1 hour. After the usual treatment, the residue is dissolved in THF: water (4:1, v/v) and treated with 2M caustic soda (1 ml).

After 3 hours, the reaction mixture is acidified to pH: 1 with 1M HCl, extracted from chloroform. The organic phases are washed with water, dried and evaporated. The residue was treated with an ether solution of diazmethane for one-half hour. After evaporation to dryness, the residue is washed on a silica gel column (2 g). Elution with the mixture hexane-AcOEt (5:2, v/v) gave the compound 22 (22 mg, 75%) colorless syrup.

NMR (CDCl$_3$):δ:3.40 (s, 3H, COOMe ido), 2.85 (1H, OH). The rest of the spectrum agrees with the expected structure.

By sulfatation (for example with an SO$_3$:Me$_3$N complex in DMF) then hydrolysis (for example by means of Pd/c in MeOH, H$_2$O) the dermatane-sulfate based unit is obtained.

EXAMPLE 3

Synthesis of a compound A having the following structure

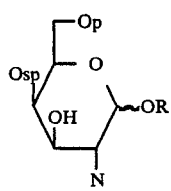

useful in a sequence (U—A)$_n$ and representing the A unit of the reductive end part of the sequence.

The unit of formula 26 is obtained according to the following steps a starting from compound 23, itself obtained according to the method of PAULSEN H. et al in Tetrahedron. Lettr. 24 (1983) 1759–1762 (see FIG. 4)

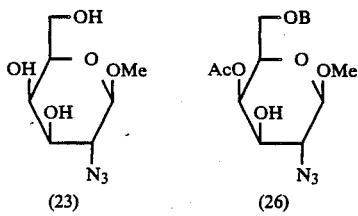

Preparation of the derivative 3,4-O-isopropylidene 24

A solution of 23 (635 mg) in anhydrous acetone (20 ml) is shaken at room temperature in the presence of p-toluenesulfonic acid (monohydrate, 40 mg) for 5 hours. Triethylamine (1 ml) is added, and the reaction mixture is evaporated to dryness. The residue is chromatographed on a silica gel column (40 g). Elution with the mixture CH$_2$Cl$_2$-AcOEt (5:1, v/v) containing 0.2% of triethylamine gives, in order of elution:

the 4,6-O-isopropylidene derivative, (202 mg, 27%) which is hydrolyzed and recrystallized to recover 23.

the expected derivative 24 (488 mg, 0.5%), F 84°–85° C. (ether-hexane), (α)$_D$ +43° (cl, CHCl$_3$). NMR spectrum in accordance with the expected structure. (AcOEt represents ethyl acetate).

Benzylation and hydrolysis of 25

A solution of 24 (520 mg) in anhydrous DMF (8 ml) is treated successively with sodium hydride (196 mg, at 50% in oil) and benzyl bromide (0.36 ml). After 1 hour, methanol (1 ml) is added with care, and the reaction mixture is evaporated to dryness. The residue is taken up again in chloroform (50 ml) and the organic phase is washed with water, dried (sodium sulfate) and evaporated.

The residue is dissolved in 90% trifluoroacetic acid (10 ml), stirred for 10 minutes at room temperature and evaporated to dryness. The residue is washed on a silica gel column (10 mg). Elution with the mixture AcOEt:-hexane (1:1, v/v) gives the derivative 25 (540 mg, 87%), a colorless syrup, (α)$_D$ +5° (cl, chloroform). NMR spectrum in accordance with the expected structure.

Selective acetylation to give the semi-open derivative 26

The diol 25 (450 mg) is shaken in a mixture of anhydrous toluene (10 ml) and trimethyl orthoacetate (1.5 ml) at room temperature. Then p-toluenesulfonic acid (monohydrate, 3 mg) is added and stirred for another hour. Triethylamine (1 ml) is added, the mixture is diluted with toluene (70 ml) and washed with water, dried (sodium sulfate) and evaporated.

The residue is dissolved in 80% acetic acid, stirred 10 minutes at room temperature, then evaporated to dryness to give quantitatively the compound 26 (485 mg, 95% from 25), syrup, (α)$_D$ −45° (cl, CHCl$_3$). NMR (CDCL$_3$) δ:7.25 (s, 5H, Ph), 5.26 (d. of d., 1H, J$_{3,4}$:3Hz, J$_{4,5}$:1Hz, H-4), 4.14 (d, 1H, J$_{1,2}$:7Hz, H-1), 3.52 (s,3H,OMe), 2.90 (d, 1H, J, 3Hz, OH).

EXAMPLE 4

Preparation of an open compound A

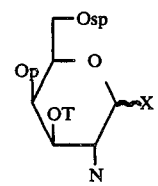

The prepared derivative has formula 31

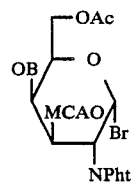

and is obtained according to steps 1 to 4 starting from compound 27

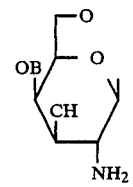

whose synthesis is disclosed by R. W. JEANLOZ et al. in JACS 76 (19654) 5682 (see FIG. 5).

N-phthalimidoylation of 28

A solution of 27 (100 mg) in methanol (1 ml) was treated at 60° C. for 1 hour with phthalic anhydride (75 mg) and triethylamine (60 μl). After cooling, the mixture was evaporated to dryness and crystallized in a CH$_2$Cl$_2$-ether-hexane mixture. The intermediate compound 2-(2'-carboxybenzamido) was dissolved in acetic anhydride (5 ml) and heated to 100° C. for 2 hours in the presence of sodium acetate (100 mg). After cooling, the mixture was poured into ice water and stirred 1 hour. After extraction with chloroform, the organic phases were washed with water, dried and evaporated. The residue was de-acetylated with sodium methylate to give 28 (101 mg, 66%), which is a syrup crystallized in ether, MP: 157° C. (α)$_D$ −82° (cl, chloroform). The NMR spectrum agreed with the expected structure.

Monochloroacetylation of 28

Compound 28 (100 mg) was treated at −20° C. with monochloroacetyl chloride in the usual manner. The reaction mixture was treated in the usual manner to give 29 (115 mg, 96%), syrup, $(\alpha)_D$ +55° (cl, $CH_2Cl_2$). The NMR spectrum agreed with the expected structure.

Acetolysis of 1,6-anhydro 29

Compound 29 (100 mg) was treated with the mixture acetic anhydride:trifluoroacetic acid (9:1, v/v, 10 ml) for 24 hours, then evaporated to dryness and dried under high vacuum to give the mixture of α, β acetates (115 mg, 99%) in the form of a syrup.

The NMR spectrum ($CDCl_3$) showed the presence of 3 singlets (6H in all) at δ2.05, 1.99 and 1.97 attributed to 6-OAc, 1-OAc α and β.

Preparation of the bromide 31

A solution of the mixture of acetates 30 (100 mg) in a mixture of dichloromethane (4.5 ml) and ethyl acetate (0.5 ml) were treated with titanium tetrabromide ($TiBr_4$, 100 mg) overnight. The usual treatment gave the bromide 31 (90 mg, 84%), colorless syrup, NMR ($CDCl_3$) 6.69 (d, 1H, $J_{1,2}$:3.5Hz, H-1). The remainder of the spectrum was in agreement with the expected structure.

This unstable compound was immediately used for the glycosylation reactions.

EXAMPLE 5

Preparation of compound A of formula 39

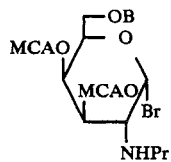

starting from derivative 32 of formula

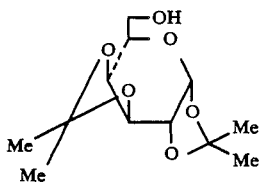

Figure 6:
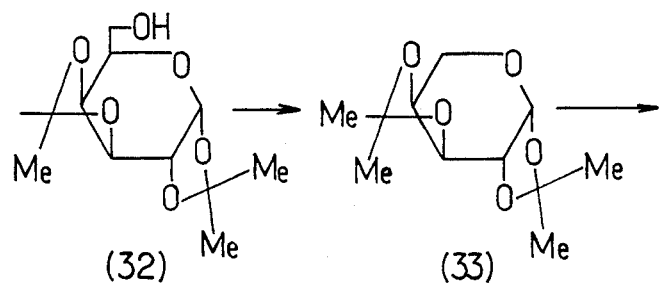
Figure 6:
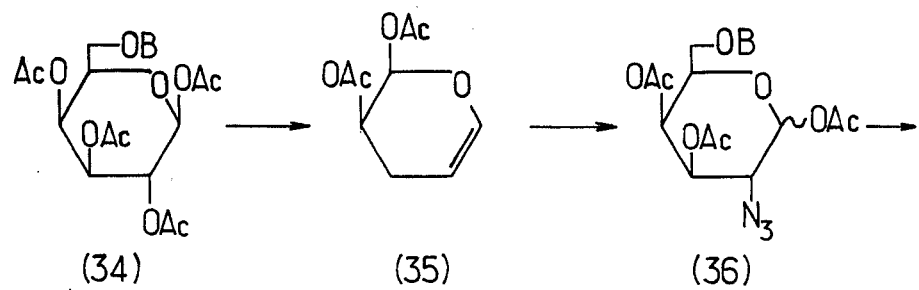
Figure 6:
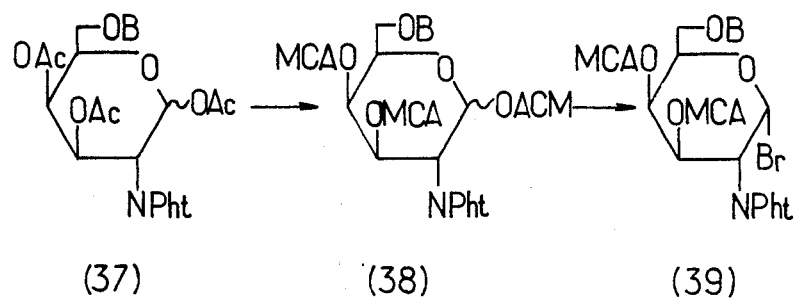

The process is carried out according to steps 1 to 7 (see FIG. 6).

(1) Benzylation of 1,2:3,4-di-O-isopropylidene-α-D-galactopyranose 32

The compound 32 (2.60 g) was benzylated in DMF (20 ml) by the action of benzyl bromide (2 ml) and sodium hydride (1 g). The usual treatment gave a residue which was distilled under vacuum to give (3.16 g, 90%), B.P.$^{0.1}$: 130°-132° C. The NMR spectrum agreed with the expected structure.

(2) Hydrolysis and acetylation of derivative 33

The derivative 33 (1 g) was dissolved in 90% trifluoroacetic acid (20 ml), shaken for 30 minutes at room temperature, then evaporated to dryness. The residue is evaporated with water (3 times 10 ml) then dried under vacuum.

The residue is dissolved in acetic anhydride (10 ml) and heated to 100° C. for 3 hours with anhydrous sodium acetate (500 mg). After cooling and the usual treatment, the residue was chromatographed on a column of silica gel (100 g). Elution with the mixture hexane-ethyl acetate (3:2, v/v) gives, in order of elution:

a fraction containing the furan isomers (480 mg, 38%), for which the α isomer is predominant (NMR:δ6.32) (d, 1H, $J_{1,5}$ Hz, $H_1^\alpha$).

a fraction containing the acetate 34 (612 mg, 49%), colorless syrup, NMR:δ5.65 (d, 1H, $J_{1,2}$ 7.5Hz, $H_1$). The remainder of the spectrum was in agreement with the expected structure.

(3) Preparation of the "galactal" 35

A solution of the acetate 34 (1 g) in ether (10 ml) is stirred at room temperature in the presence of benzylamine (1 ml) for 2 hours. After dilution with dichloromethane (50 ml), the organic phase was washed with iced 0.1M HCl, with water, dried (sodium sulfate) and evaporated.

The residue (reducing product, free on the anomeric carbon) is dissolved in anhydrous dichloromethane (10 ml) and treated with an excess of dimethylbromoforminium bromide (brominated Vilsmeier reagent) in the presence of symcollidine (0.5 ml) for 1 hour at room temperature. The usual treatment gave the unstable intermediate α-bromo derivative, which was directly used for the elimination reaction (885 mg, 81%). NMR:δ:7.25 (m, 5H, Ph), 6.31 (d, 1H, $J_{1,2}$ 3.5Hz, H-1).

A solution of the bromide (885 mg, freshly prepared) in acetic acid (5 ml) was added drop by drop at 0° to a mixture of acetic acid (4 ml), water (15 ml), sodium acetate (2 g), powdered zinc (1 g) and $CuSO_4$, $5H_2O$ (0.1 g). After 4 hours vigorous stirring at 0° C., the mixture was filtered, the filtrate diluted with water, extracted chloroform (3 times 20 ml). The organic phase was washed with water, dried (sodium sulfate) and evaporated. The residue was washed on a silica gel column (50 g). Elution with the mixture hexane-ethyl acetate (5:3, v/v) gave the galactal 35, colorless syrup (595 mg, 55%); the NMR spectrum was in agreement with the expected structure.

(4) Azidonitration of the galactal 35

A solution of the galactal 35 (1 g) in anhydrous acetonitrile (10 ml) was shaken at −20° C. in a dry argon atmosphere in the presence of sodium azide (200 mg) and cerium-ammonium nitrate (3.5 g) for 12 hours. After dilution with cold ether (50 ml), the organic phase was washed with water, dried (sodium sulfate) and evaporated. The residue (containing principally the mixture of α, β nitrates) was immediately dissolved in acetic acid (10 ml and heated to 100° in the presence of anhydrous sodium acetate (400 mg) for 1 hour. The usual treatment gave a residue which was chromatographed on a silica gel column (50 g). Elution by the mixture toluene-ethyl acetate (8:1; v/v) gave the mixture of acetates 35 (760 mg, 51% from 35), which contains predominantly the α-acetate, NMR δ7.28 (s, 5H, Ph), 6.22 (d, 1H, $J_{1,2}$ 3.5Hz, $H_1^\alpha$).

(5) Preparation of the N-phthalimido derivative 37

The mixture of acetates 36 (200 mg) was dissolved in ethanol (10 ml) containing $NiCl_2$, $6H_2O$ (0.4 g) and boric acid $H_3BO_3$ (0.2 g). Then drop by drop a solution of $NaBH_4$ in ethanol (10 mg/ml) was added until the disappearance of the green color and the appearance of a gray-black color. The mixture was then evaporated to dryness and diluted with water, then extracted with chloroform (5 times 10 ml). The organic phase was washed with water, dried (sodium sulfate) and evaporated.

The residue (2-amino derivative, giving a pink spot by vaporization of ninhydrin in t.l.c.) was immediately treated in methanol (3 ml) with phthalic anhydride (150 mg) in the presence of triethylamine (120 l) at 60° for 2 hours. After the usual treatment, the residue was treated at 100° for 2 hours with acetic anhydride (10 ml) and sodium acetate (200 mg). After treatment the residue obtained was chromatographed on a silica gel column (15 g). Elution with the mixture ethyl acetate-hexane (1:1, v/v) gave the mixture of acetates 37 (152 mg, 66%). The NMR spectrum agreed with the expected structure. The IR spectrum showed the total absence of the "Azid" band.

(6) Preparation of the derivative 38

The mixture of acetates 37 (150 mg) was de-acetylated conventionally at 0° C. (MeONa in methanol). The residue was monochloroacetylated at −20° C. in a pyridinedichloromethane mixture in the usual way, to give the mixture of anomeric α, β, monochloroacetates, a syrup (155 mg, 87%). The NMR spectrum was in agreement with the expected structure.

(7) Preparation of the bromide 39

A solution of the mixture of monochloroacetates 38 (100 mg) in dichloromethane (5 ml) and ethyl acetate (0.5 ml) was treated at room temperature with titanium tetrabromide (TiBr$_4$, 100 mg) for 16 hours. The usual treatment gave the bromide 39 (76 mg, 75%), an unstable syrup. NMR δ8.0–7.10 (m, 9H, aromatic), 6.59 (d, 1H, J$_{1,2}$:3.5Hz, H-1). The remainder of the spectrum agreed with the expected structure. This "activated" compound was immediately used for the subsequent glycosylation reactions.

EXAMPLE 6

Preparation of a semi-open compound "U—A" of the type

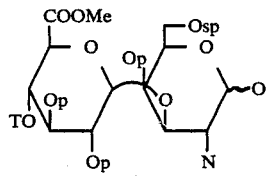

Part A is a semi-open unit useful for chondroitin-6-sulfates and is prepared according to the scheme:

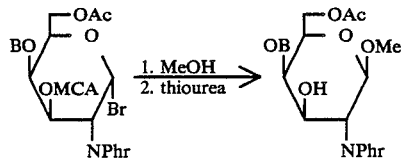

Part U is obtained from:

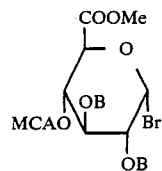

Figure 7:
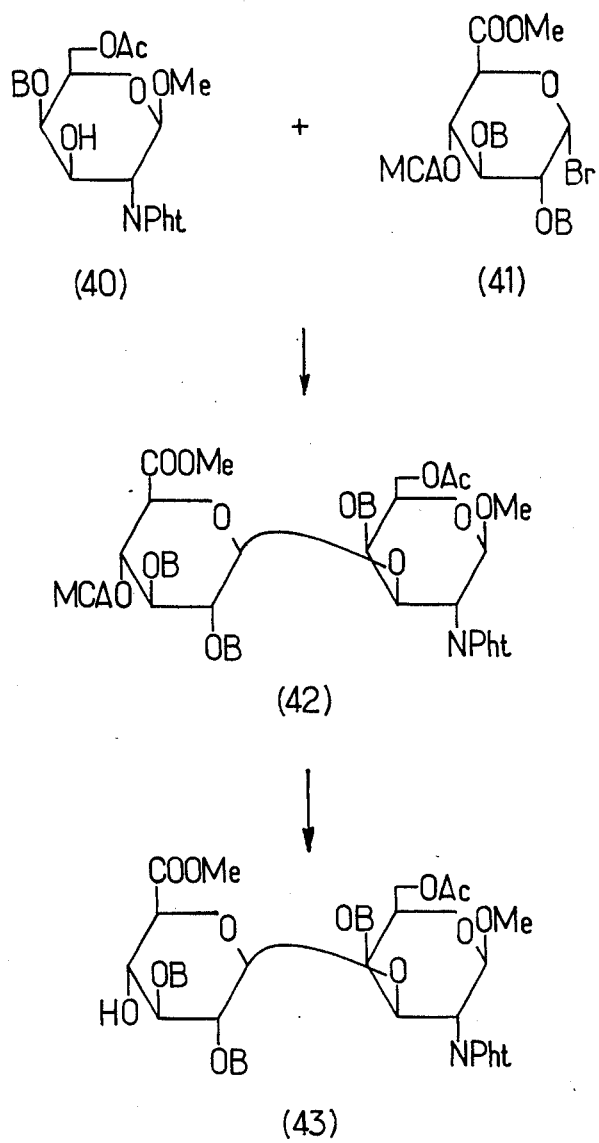

The coupling is carried out according to the scheme of FIG. 7 to give disaccharide 43

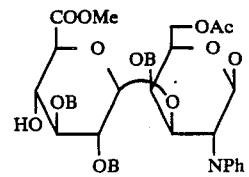

Synthesis of 40 from the bromide 27

A solution of the bromide 27 (200 mg) in anhydrous dichloromethane (3 ml) is stirred shielded from light and moisture in the presence of silver silicate (300 mg), molecular sieve 4 Å in powder form (100 mg) and methanol (0.25 ml) for 5 hours at ambient temperature. The solids were filtered, rinsed with dichloromethane, and the filtrate was evaporated.

The residue was de-O-monochloroacetylated with thiourea in the pyridine-ethanol mixture in the usual manner. The residue was washed on a silica gel column (15 g). Elution by the mixture AcOEt-hexane (2:1, v/v) gave the derivative 40 (122 mg, 78%), colorless syrup.

NMR:δ3.60 (s, 3H, OMe), 2.30 (1H, OH, exchangeable with D$_2$O), 2.06 (s, 3H, OAc).

Condensation with the units 40 and 41

A solution of the bromide 41 (158 mg) and alcohol 40 (91 mg) in anhydrous dichloromethane (5 ml) is stirred at room temperature protected from light and moisture in the presence of freshly prepared silver carbonate (120 mg) and of 4 Å molecular sieve in powder form (200 mg) for 3 days.

The solids were filtered, the filtrate was evaporated and the residue was chromatographed on a silica gel column (20 g). Elution with the mixture AcOEt:hexane (1:1, v/v) gives disaccharide 42 (106 mg, 52%), syrup.

The NMR spectrum agreed with the structure: δ:3.70 (s, 3H, COOMe), 3.50 (s, 3H, OMe), 2.04 (s, 3H, OAc).

De-O-monochloroacetylation of 42

The disaccharide 42 (80 mg) was de-O-monochloroacetylate· with hydrazine-dithiocarbonate (H.D.T.C.) by the method described by C. A. van BOECHEL and T. BEETZ, *Tetrahedron, Letters*, 24 (1983) 3775. After treatment, the residue was washed on a silica gel column (5 g). Elution with the mixture AcOEt-hexane (2:1, v/v) gave the semi-open disaccharide 43 (67 mg, 90%, syrup.

NMR:δ8.0–7.10 (m, 19H, aromatic), 3.74 (s, 3H, COOMe), 3.46 (s, 3H, OMe), 2.70 (1H, OH, exchangeable with D$_2$O), 1.98 (s, 3H, OAc).

EXAMPLE 7

Synthesis of semi-open derivatives A—U of the type

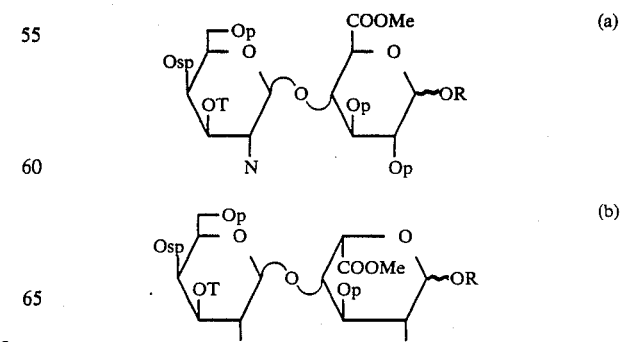

Said compounds are useful for chondroitin-4-sulfates (a) and dermatane-sulfate (b). A units are prepared starting from 39. U units correspond to products 13 and 115 of FR patent application No. 82 18003 of Oct. 27, 1982 in the name of the applicant. In this application, they are respectively numbered 44 and 45. Reference will be made to FIG. 8.

(a) Preparation of a derivative of the a type: the process is carried out according to the following steps 1 and 2

(1) Condensation reaction for the preparation of 45

A solution of 39 page 6 (124 mg) and of 44 (64 mg) in anhydrous dichloromethane (3 ml) was stirred at −20° in the presence of a 4 Å molecular sieve in powder form (100 mg) under a dry argon atmosphere. Then successively there were added sym-collidine (0.10 ml) and silver sulfate (70 mg), and the temperature allowed to rise again to the ambient temperature overnight. The solids were drained, washed with dichloromethane, the filtrate is washed with 0.1M HCl, with water, with 5% $NaHCO_3$, with water, dried (sodium sulfate) and evaporated. The residue was chromatographed on a silica gel column (20 g). Elution by the mixture hexane:AcOEt (2:1, v/v) gave the disaccharide 45 (110 mg, 70%), syrup.

NMR:δ3.98 and 3.96 (2s, 4H, 2 Cl–$CH_2$COO), 3.72 (s, 3H, COOMe). The remainder of the spectrum agreed with the expected structure.

Synthesis of the semi-open disaccharide 47

The disaccharide 45 (100 mg) was de-O-monochloroacetylated by hydrazine dithiocarbonate as described previously. The disaccharide diol obtained was found in the toluene (5 ml) through trimethylorthoacetate (1 ml) in the presence of p-toluenesulfonic acid (1 mg) for 2 hours; then the orthoester formed was treated with 80% acetic acid for 10 minutes at room temperature. After evaporation to dryness, the semi-open derivative 47 was obtained (72 mg, 80%), colorless syrup.

NMR:δ:8.0–7.10 (m, 19H, aromatics), 5.25 (d. of d., 1H, $J_{3,4}$:3Hz, $J_{4,5}$:1Hz, H'-4), 3.73 (s, 3H, COOMe), 2.70 (1H, OH, exchangeable with $D_2O$), 2.01 (s, 3H, oAc).

(b) Preparation of a derivative of the b type

Condensation reaction for the preparation of 48

The compounds 39 (124 mg) and 45 (60 mg) were condensed and treated in the manner described for the preparation of 46 to give the disaccharide 47 (102 mg, 72%), syrup.

NMR:δ8.0–7.15 (m, 19H, aromatics), 3.98 and 3.94 (2s, 4H, 2 Cl.$CH_2$COO), 3.65 (s, 3H, COOMe, 3.46 (s, 3H, oMe).

Synthesis of the semi-open derivatives 49

The disaccharide 48 (80 mg) was treated as previously for the preparation of the derivative 47 to give 49 (56 mg, 78%), syrup.

NMR:δ5.22 (d. of d., 1H, $J_{3,4}$:3Hz, $J_{4,5}$:1Hz, H'-4), 3.62 (s, 3H, COOMe), 3.42 (s, 3H, OMe), 2.55 (1H, OH, exchangeable with $D_2O$), 1.97 (s, 3H, OAc).

EXAMPLE 8

Synthesis of a semi-open derivative of the A—U type

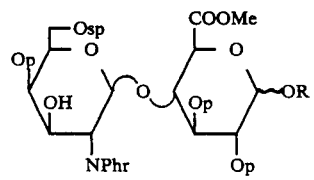

Such compounds are useful for chondroitin-6-sulfates.

A unit is prepared starting from compound 27 and U unit corresponds to compound 13 of said FR patent application, which is herein numbered 44.

Figure 9:
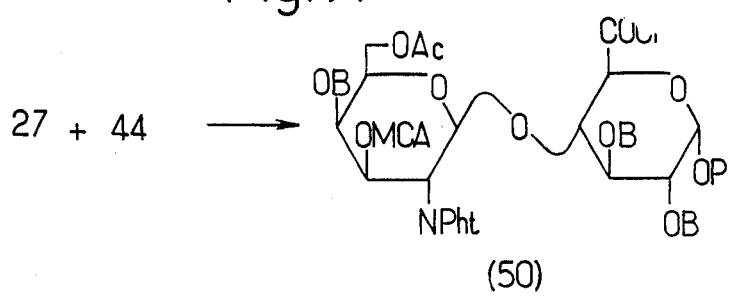
Figure 9:
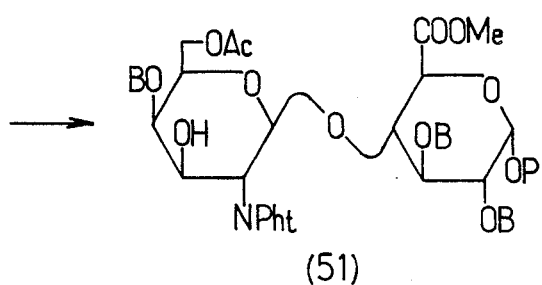
Figure 10:
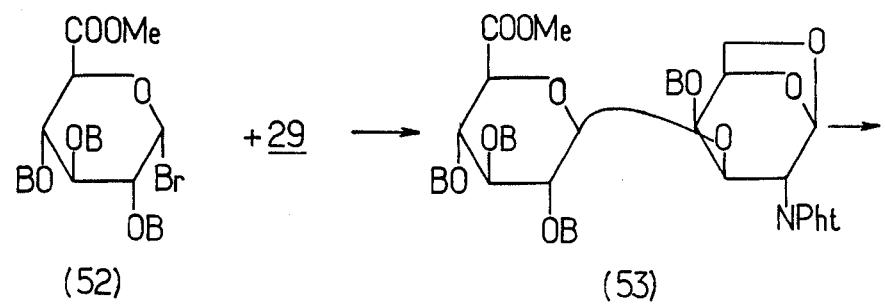
Figure 10:
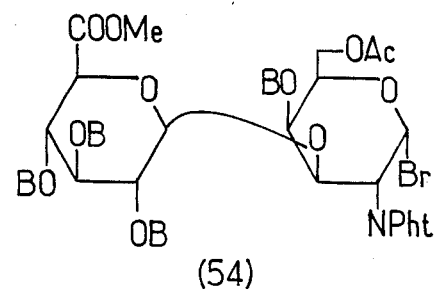
Figure 11:
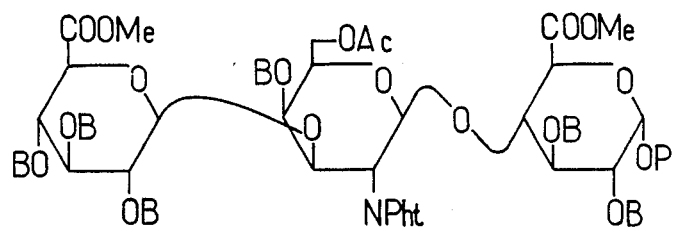

Disaccharide 51 is prepared as follows (see FIG. 9)

Condensation reaction for the preparation of 50

The mixture of 44 (64 mg) and the bromide 27 (116 mg) was obtained exactly in the way described for the preparation of the disaccharide 46.

The residue was chromatographed on a silica gel column (25 g). Elution with the mixture hexane-AcOEt (5:2, v/v) gave the disaccharide 50 (112 mg, 74%), syrup.

NMR:δ8.05–7.15 (m, 19H, aromatics), 3.97 (s, 2H, Cl–$CH_2$COO), 3.75 (s, 3H, COOMe), 2.07 (s, 3H, oAc). The rest of the spectrum agreed with the expected structure.

De-O-monochloroacetylation of disaccharide 50

The disaccharide 50 (95 mg) was de-O-monochloroacetylated with thiourea in the mixture pyridine-ethanol. After purification on a silica gel column (5 g) and elution by the mixture hexane-AcOEt (4:3, v/v), the semi-open disaccharide 51 was obtained (64 mg, 72%), syrup.

NMR:δ8.0–7.10 (m, 19H, aromatics), 3.78 (s, 3H, COOMe), 2.85 (1H, OH, exchangeable with $D_2O$), 2.06 (s, 3H, OAc).

EXAMPLE 9

Synthesis of a trisaccharide U—A—U of the type

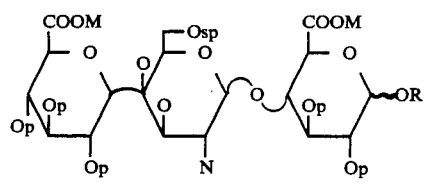

Such trisaccharides are useful for chondroitin-6-sulfates. The synthesis scheme is given on FIGS. 10 and 11. Compound 52 is prepared according to the method of R. R. Schmidt et al. in Tetrahedron Letters, 21 (1980) 1421.

Synthesis of the disaccharide 53

A solution of the alcohol 29 (76 mg) and the bromide 52 (216 mg) in anhydrous dichloromethane (5 ml) was stirred for 4 days at ambient temperature protected from the light in the presence of freshly prepared silver carbonate (160 mg) and 4 Å molecular sieve in powder form (200 mg). After filtration and evaporation, the residue was chromatographed on a silica gel column (30 g). Elution with the mixture hexane-ethyl acetate (2:1, v/v) gave the disaccharide 53 (87 mg, 52%), syrup.

NMR:δ8.0–7.15 (m, 24H, aromatics), 3.74 (s, 3H, COOMe), 5.32 (s, wide, H-1).

Acetolysis and bromination of the disaccharide 53

The disaccharide 53 (100 mg) was acetolysed with the mixture acetic anhydride:trifluoroacetic acid (9:1, v/v, 5 ml) overnight. After evaporation to dryness, the residue (mixture of the anomeric acetates) was treated withbenzylamine in ether as previously described to give the reducing disaccharide (free on the anomeric "A" carbon atom) which was immediately treated with dimethylbromoformiminium bromide in the presence of symcollidine to give the bromide 54 (78 mg, 68%), unstable syrup used immediately.

NMR:δ6.41 (d, 1H, $J_{1,2}$3.5Hz, H-1), 2.05 (s, 3H, oAc). The rest of the spectrum agreed with the expected structure.

Condensation for the preparation of the trisaccharide 55

The alcohol 44 (43 mg) and the halide 54 (144 mg) were condensed by the silver sulfate method as described for the disaccharide 46. The residue was chromatographed on a silica gel column (20 g). Elution with the mixture AcOEt:hexane (1:1, v/v) gave the disaccharide 55 (163 mg, 53%).

NMR:δ7.95–7.10 (m, 34H, aromatics), 3.74 and 3.71 (2s, 2×3H, 2 COOMe), 2.05 (s, 3H, oAc). The remainder of the spectrum is in agreement with the expected structure.

EXAMPLE 10

Synthesis of a tetrasaccharide of the type U—A—U—A

A tetrasaccharide of the following formula is prepared

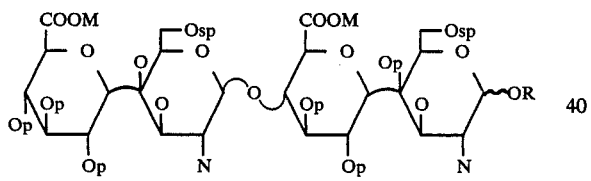

Figure 12:
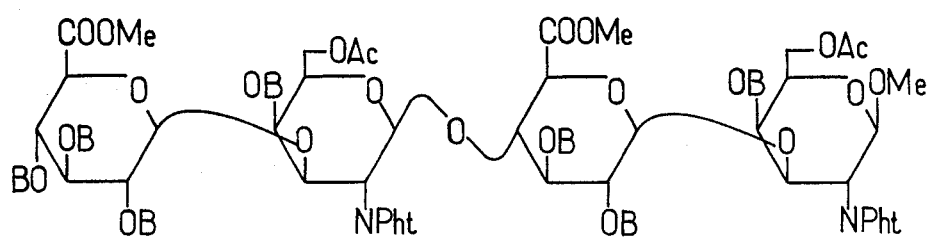

Tetrasaccharide 56 is prepared by using disaccharides 54 and 43 according to the following step (see FIG. 12).

The compounds 54 (96 mg) and 43 (90 mg) were condensed by the silver sulfate method as previously described for the disaccharide 45. The residue was chromatographed on the silica gel column (20 g). Elution with the mixture hexane-AcOEt (4:3, v/v) gave the tetrasaccharide 56 (82 mg, 46%), colorless glass.

NMR:δ:8.10–7.05 (m, 43H, aromatics), 3.77 and 3.70 (2s, 2×3H, 2 COOMe), 3.46 (s, 3H, OMe), 2.08 and 2.04 (2s, 2×3H, 2 OAc).

We claim:

1. A process for synthesizing an acid mucopolysaccharide condensation product having from 2–12 saccharides which process comprises condensing a first saccharide with a second saccharide to form a condensation product having a 1–4 beta linkage between the first saccharide and the second saccharide,
    wherein the first saccharide is selected from the group consisting of a protected D-galactosamine unit and an oligosaccharide comprised of alternating protected D-galactosamine and protected uronic acid units linked in the manner found in chondroitin sulfate and dermatan sulfate and having a terminal D-galactosamine at the reducing end, and
    wherein the second saccharide is selected from the group consisting of a uronic acid unit and an oligosaccharide comprised of alternating protected D-galactosamine and protected uronic acid units linked in the manner found in chondroitin sulfate and dermatan sulfate and having a terminal uronic acid at the now reducing end, further
    wherein any uronic acid unit is selected from the group consisting of D-glucuronic acid and L-iduronic acid and further
    wherein any D-galactosamine units have nitrogen containing groups at carbon 2, which nitrogen containing groups can be treated to form an amine.

2. A process for synthesizing a protected acid mucopolysaccharide condensation product having from 2–12 saccharide units and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-galactosamine units, which process comprises the step of condensing a first protected saccharide with a second protected saccharide to form a protected condensation product,
    wherein the first protected saccharide is selected from the group consisting of a protected D-galactosamine unit and an oligosaccharide comprised of alternating protected D-galactosamine and protected uronic acid units linked in the manner found in chondroitin sulfate and dermatan sulfate and having a terminal D-galactosamine at the reducing end, further wherein the first protected saccharide has a reactive group as a substituent at carbon 1 at the reducing end which reactive group allows a stereospecific linkage during the condensation, and
    wherein the second protected saccharide is selected from the group consisting of a protected uronic acid unit and an oligosaccharide comprised of alternating protected D-galactosamine and protected uronic acid units linked in the manner found in chondroitin sulfate and dermatan sulfate and having a terminal uronic acid at the nonreducing end,
    wherein any uronic acid units are selected from the group consisting of D-glucuronic acid and L-iduronic acid, and
    wherein the protected condensation product formed has a 1–4 beta linkage between the first protected saccharide and the second protected saccharide, the protected condensation product further having at least one each of semi-permanent protecting groups, permanent protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during the removal of the semi-permanent protecting groups and the introduction of functional groups to replace the semi-permanent protecting groups, which functional groups are selected from the group consisting of —O—SO₃ groups and —O—PO₃ groups, and which permanent protecting groups also are removable in the presence of the functional groups, are stable during the condensation, and allow a stereospecific linkage during the condensation, and which other protecting groups form an ester at the carboxyl groups of the uronic acid units and are stable during the condensation, and which nitrogen containing groups are substituents at carbon 2 of the D-galactosamine units, can be treated to form an amine, are stable during the condensation, and allow a stereospecific linkage during the condensation.

3. A process for synthesizing a protected acid mucopolysaccharide condensation product having from 2–12 saccharide units and having semi-permanent protecting groups and permanent protecting groups as substituents at carbon positions thereon to allow selective positioning of functional groups at desired positions, further having other protecting groups which form an ester at the carboxyl groups and having nitrogen containing groups as substituents at position 2 of D-galactosamine units, which process comprises condensing a first protected saccharide with a second protected saccharide to form a protected condensation product wherein the first protected saccharide is selected from the group consisting of a protected uronic acid unit and an oligosaccharide comprised of alternating protected D-galactosamine and protected uronic acid units linked in the manner found in chondroitin sulfate and dermatan sulfate and having a terminal uronic acid at the reducing end, further wherein the first protected saccharide has a reactive group as a substituent at carbon 1 at the reducing end which reactive group allows a stereospecific linkage during the condensation, and wherein the second protected saccharide is selected from the group consisting of a protected D-galactosamine unit and an oligosaccharide comprised of alternating protected D-galactosamine and protected uronic acid units linked in the manner found in chondroitin sulfate and dermatan sulfate and having a terminal D-galactosamine at the nonreducing end, wherein any uronic acid units are selected from the group consisting of D-glucuronic acid and L-iduronic acid, and wherein the protected condensation product formed has a 1–3 beta linkage between the first protected saccharide and the second protected saccharide where the first protected saccharide is a D-glucuronic acid or an oligosaccharide having a terminal D-glucuronic acid, and wherein the protected condensation product formed has a 1–3 alpha linkage between the first protected saccharide and the second protected saccharide where the first protected saccharide is an L-iduronic acid or an oligosaccharide having a terminal L-iduronic acid, the protected condensation product further having at least one each of semi-permanent protecting groups, permanent protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during the removal of the semi-permanent protecting groups and the introduction of functional groups to replace the semi-permanent protecting groups, which functional groups are selected from the group consisting of —O—SO₃ groups and —O—PO₃ groups, and which permanent protecting groups also are removable in the presence of the functional groups, are stable during the condensation, and allow a stereospecific linkage during the condensation, and which other protecting groups form an ester at the carboxyl groups of the uronic acid units, and are stable during the condensation, and which nitrogen containing groups are substituents at carbon 2 of the D-galactosamine units, can be treated to form an amine, are stable during the condensation, and allow a stereospecific linkage during the condensation.

4. A process for synthesizing a protected acid mucopolysaccharide condensation product having from 2–12 saccharide units and having semi-permanent protecting groups and permanent protecting groups as substituents at carbon positions thereon to allow selective positioning of functional groups at desired positions, further having other protecting groups which form an ester at the carboxyl groups and further having nitrogen containing groups as substituents at position 2 of D-galactosamine units which process comprises a first step of condensing a first protected saccharide with a second protected saccharide having a 1,6 anhydro group, to form a protected condensation product wherein the first protected saccharide is selected from the group consisting of a protected uronic acid unit and an oligosaccharide comprised of alternating protected D-galactosamine and protected uronic acid units linked in the manner found in chondroitin sulfate and dermatan sulfate and having a terminal uronic acid at the reducing end, further wherein the first protected saccharide has a reactive group as a substituent at carbon 1 at the reducing end which reactive group allows a stereospecific linkage during the condensation, wherein any uronic acid units are selected from the group consisting of D-glucuronic acid and L-iduronic acid, and wherein the second protected saccharide is a D-galactosamine precursor, which D-galactosamine precursor has a 1,6 anhydro group, and wherein the protected condensation product formed has a 1–3 beta linkage between the first protected saccharide and the second protected saccharide where the first protected saccharide is a D-glucuronic acid or an oligosaccharide having a terminal D-glucuronic acid, and wherein the protected condensation product formed has a 1–3 alpha linkage between the first protected saccharide and the second protected saccharide where the first protected saccharide is a L-iduronic acid or an oligosaccharide having a terminal L-iduronic acid, the protected condensation product further having protecting groups which are selected from the group consisting of semi-permanent protecting groups and permanent protecting groups, the protected condensation product further having other protecting groups which form an ester at the carboxyl, nitrogen containing groups, and a 1,6 anhydro group as substituents at carbon positions thereon, which protecting groups, other protecting groups, nitrogen containing groups, and 1,6 anhydro group were present on the first protected saccharide and second protected saccharide, further comprising the step of treating the 1,6 anhydro precursor group to form semi-permanent protecting groups or permanent protecting groups at carbons 1 and 6, which semi-permanent protecting groups are removable in the presence of permanent protecting groups, are stable during the condensation, and allow a stereospecific linkage during the condensation, which permanent protecting groups are stable and do not migrate to different carbon positions during the removal of the semi-permanent protecting groups and the introduction of functional groups to replace the semi-permanent protecting groups, which functional groups are selected from the group consisting of —O—SO$_3$ groups and —O—PO$_3$ groups, and which permanent protecting groups also are removable in the presence of the functional groups, and allow a stereospecific linkage during the condensation, and which other protecting groups form an ester at the carboxyl groups of the uronic acid units and are stable during the condensation, which nitrogen containing groups occupy carbon 2 of the D-galactosamine units, can be treated to form an amine, are stable during the condensation and allow a stereospecific linkage during the condensation.

5. A process as in claim 1, 2 or 3 wherein the functional groups are —O—SO$_3$ groups.

6. A process as in claim 5 wherein the semi-permanent protecting groups are substituents at one or more carbon positions at any of carbons 4 and 6 of the D-galactosamine units, and carbons 2 and 3 of uronic acid units, and wherein the permanent protecting groups are substituted at positions at any of carbons 4 and 6 of the D-galactosamine units and carbons 2 and 3 of the uronic acid units which are not substituted by the semi-permanent protecting groups.

7. The process of claim 6 wherein
 (a) The nitrogen containing groups are selected from the group consisting of
  1. N$_3$,
  2. NH—lower acyl, and
  3. N-phthalimido;
 (b) the protecting groups at the carboxyl are selected from the group consisting of
  1. lower alkyl, and
  2. lower aryl;
 (c) the semi-permanent protecting groups are —O—lower acyl;
 (d) the permanent protecting groups are —O—benzyl; and
 (e) the reactive group is selected from the group consisting of
  1. halogen,
  2. o-lower imidoyl, and
  3. an orthoester formed between carbon 1 and carbon 2 of uronic acid.

8. The process of claim 7 wherein
 (a) The nitrogen containing groups are selected from the group consisting of
  1. N$_3$,
  2. NH—acetyl, and
  3. N-phthalimido;

(b) the protecting groups which forms an ester at the carboxyl are methyl;
 (c) the semi-permanent groups are —O—acetyl;
 (d) the permanent protecting groups are —O—benzyl; and
 (e) the reactive group is selected from the group consisting of
  1. Br,
  2. Cl,
  3. an orthoester having between 3 and 6 carbons, and
  4. OC(NH)CCl$_3$.

9. A process according to claim 3 wherein the second protected saccharide is a D-galactosamine precursor and contains a 1,6 anhydro group, wherein the 1,6 anhydro group is treated with an acetolysing agent to obtain —O—acetyl semi-permanent protecting groups.

10. A process according to claim 9 further comprising the step of removing the —O—acetyl group at carbon 1 of D-galactosamine and replacing it with a reactive group in order to allow the protected condensation product to be elongated.

11. A process according to claim 10 wherein the reactive group is selected from the group consisting of bromine and chlorine.

12. A process as in claim 1 or 2 wherein the carbon 1 at the reducing end of the protected condensation product is substituted by a protecting group which is selected from the group consisting of a semi-permanent protecting group and a permanent protecting group.

13. A process as in claim 1 or 2 wherein the carbon 4 of any uronic acid at the non-reducing end of the protected condensation product, or the carbon 3 of any D-galactosamine at the non-reducing end of the protected condensation product is substituted by a protecting group which is selected from the group consisting of a semi-permanent protecting group and a permanent protecting group.

14. A process as in claim 1 or 2 further wherein the carbon 1 at the reducing end of the protected condensation product is substituted by an inert protecting group, which inert protecting group is stable during the condensation and during removal of the permanent protecting groups.

15. A process for synthesizing a protected mucopolysaccharide condensation product having from 2-12 saccharide units which can be elongated, and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-galactosamine units, and further having temporary protecting groups positioned thereon to allow elongation of the protected condensation product, which process comprises condensing a first protected saccharide with a second protected saccharide to form a protected condensation product wherein the first protected saccharide is selected from the group consisting of a protected D-galactosamine unit and an oligosaccharide comprised of alternating protected D-galactosamine and protected uronic acid units linked in the manner found in chondroitin sulfate and dermatan sulfate and having a terminal D-galactosamine at the reducing end, further wherein the first protected saccharide has a reactive group as a substituent at carbon 1 at the reducing end which reactive group allows a stereospecific linkage during the condensation, and wherein the second protected saccharide is selected from the group consisting of a protected uronic acid unit and an oligosaccharide comprised of alternating protected D-galactosamine and protected uronic acid units linked in the manner found in chondroitin sulfate and dermatan sulfate and having a terminal uronic acid at the nonreducing end, wherein any uronic acid is selected from the group consisting of D-glucuronic acid and L-iduronic acid, and wherein the protected condensation product has a 1-4 beta linkage between the first protected saccharide and the second protected saccharide, the protected condensation product further having at least one each of semi-permanent protecting groups, permanent protecting groups, temporary protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during introduction of functional groups to replace the semi-permanent protecting groups, which functional groups are selected from the group consisting of —O—SO$_3$ groups and —O—PO$_3$ groups, and which permanent protecting groups also are removable in the presence of the functional groups, are stable during the condensation, and which allow a stereospecific linkage during the condensation, which other protecting groups form an ester at the carboxyl groups of the uronic acid units and are stable during the condensation, which temporary protecting groups are substituted at any of carbon 1 at the reducing end of the protected condensation product, carbon 4 of any uronic acid at the non-reducing end of the protected condensation product, and carbon 3 of any D-galactosamine at the non-reducing end of the protected condensation product, and which temporary groups are removable in the presence of the semi-permanent protecting groups and permanent protecting groups in order to permit elongation of the protected condensation product, and which nitrogen containing groups are substituents at carbon 2 of the D-galactosamine units, can be treated to form an amine, are stable during the condensation, and allow a stereospecific linkage during the condensation.

16. A process for synthesizing a protected mucopolysaccharide condensation product having from 2-12 saccharide units which can be elongated, and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-galactosamine units, and further having temporary groups positioned theron to allow elongation of the protected condensation product, which process comprises condensing a first protected saccharide with a second protected saccharide to form a protected condensation product wherein the first protected saccharide is selected from the group consisting of a protected uronic acid unit and an oligosaccharide comprised of alternating protected D-galactosamine and protected uronic acid unit linked in the manner found in chondroitin sulfate and dermatan sulfate and having a terminal uronic acid at the reducing end, further wherein the first protected saccharide has a reactive group as a substituent at carbon 1 at the reducing end which reactive group allows a stereospecific linkage during the condensation, and wherein the second protected saccharide is selected from the group consisting of a protected D-galactosamine unit and an oligosaccharide comprised of alternating protected D-galactosamine and protected uronic acid units linked in the manner found in chondroitin sulfate and dermatan sulfate and having a terminal D-galactosamine at the nonreducing end, whererin any uronic acid is selected from the group consisting of D-glucuronic acid and L-iduronic acid, and wherein the protected condensation product has a 1-3 beta linkage between the first protected saccharide and the second protected saccharide where the first protected saccharide is a D-glucuronic acid unit or an oligosaccaride having a terminal D-glucuronic acid, and a 1-3 alpha linkage between the first protected saccharide and the second protected saccharide where the first protected saccharide is an L-iduronic acid unit or an oligosaccharide having a terminal L-iduronic acid, the protected condensation product further having at least one each of semi-permanent protecting groups, permanent protecting groups, temporary protecting groups, other protecting groups, and nitrogen containing groups thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during introduction of functional groups to replace the semi-permanent protecting groups, which functional groups are selected from the group consisting of —O—SO$_3$ groups and —O—PO$_3$ groups, and which permanent protecting groups also are removable in the presence of the functional groups, are stable during the condensation, and which allow a stereospecific linkage during the condensation, which other protecting groups which form an ester at the carboxyl groups of the uronic acid units are stable during the condensation, which temporary protecting groups ae substituted at any of carbon 1 at the reducing end of the protected condensation product, carbon 4 of any uronic acid at the non-reducing end of the protected condensation product, and carbon 3 of any D-galactosamine at the non-reducing end of the protected condensation product, and which temporary groups are removable in the presence of the semi-permanent protecting groups and permanent protecting groups in order to permit elongation of the protected condensation product, and which nitrogen containing groups are substituents at carbon 2 of the D-galactosamine units, can be treated to from an amine, are stable during the condensation, and allow a stereospecific linkage during the condensation.

17. A process as in claim 15 or 16 wherein the functional groups are —O—SO$_3$ groups.

18. A process as in claim 15 or 16 wherein the semi-permanent protecting groups are substituted at one or more carbon positions at any of carbons 4 and 6 of D-galactosamine units, and carbons 2 and 3 of uronic acid units and wherein the permanent protecting groups are substituted at positions at any of carbons 4 and 6 of the D-galactosamine units and carbons 2 and 3 of the uronic acid units which are not substituted by the semi-permanent protecting groups.

19. A process according to claim 18 further comprising the steps of removing a temporary protecting group at the reducing end of the protected condensation product, substituting a reactive group and performing a second condensation to form an elongated protected condensation product comprised of alternating protected D-galactosamine and protected uronic acid units linked in the manner found in chondroitin sulfate and dermatan sulfate and having protecting groups thereon.

20. A process according to claim 18 further comprising the steps of removing a temporary group at the non-reducing end of the protected condensation product and performing a second condensation to form an elongated condensation product comprised of alternating protected D-galactosamine and protected uronic acid units linked in the manner found in chondroitin sulfate and dermatan sulfate and having protecting groups thereon.

21. The process of claim 18 wherein
(a) The nitrogen containing groups are selected from the group consisting of
 1. N$_3$,
 2. NH—lower acyl, and
 3. N-phthalimido;.
(b) the protecting groups at the carboxyl are selected from the group consisting of
 1. lower alkyl, and
 2. lower aryl;
(c) the semi-permanent protecting groups are —O-lower acyl;
(d) the permanent protecting groups are —O-benzyl; and
(e) the reactive group is selected from the group consisting of
 1. halogen
 2. o-lower imidoyl, and
 3. an orthoester formed between carbon 1 and carbon 2 of uronic acid,
(f) the temporary group is selected from the group consisting of
 1. —O-lower acyl,
 2. —O-allyl,
 3. —O-propenyl, and
 4. halogenated —O-lower acyl.

22. The process of claim 21 wherein
(a) The nitrogen containing groups are selected from the group consisting of
 1. N$_3$,
 2. NH—acetyl, and
 3. N-phthalimido;

(b) The protecting groups which forms an ester at the carboxyl are methyl;
(c) The semi-permanent groups are —O-acetyl;
(d) The permanent protecting groups are —O-benzyl; and
(e) the reactive group is selected from the group consisting of
 1. Br,
 2. Cl,
 3. an orthoester having between 3 and 6 carbons, and
 4. OC(NH)CCl$_3$;
(f) The temporary protecting groups are selected from the group consisting of
 1. —O-acetyl,
 2. —O-allyl,
 3. —O-propenyl,
 4. monochloro—O-acetyl, and
 5. trichloro—O-acetyl.

23. A process for selectively positioning sulfate groups or phosphate groups on a protected acid mucopolysaccharide having from 2–12 units, which acid mucopolysaccharide is comprised of alternating protected D-galactosamine and protected uronic acid units linked in the manner found in chondroitin sulfate and dermatan sulfate and having at least one each as substituents of semi-premanent protecting groups, permanent protecting groups, other protecting groups which form an ester at the carboxyl groups of the uronic acid units, and nitrogen containing groups at carbon 2 of the D-galactosamine units, wherein the permanent protecting groups are stable and do not migrate to other carbon positions during removal of the semi-permanent protecting groups and the introduction of functional groups, and wherein any uronic acid units are selected from the group consisting of D-glucuronic acid and L-iduronic acid, which process comprises the steps of
(a) removing the semi-permanent protecting groups,
(b) introducing functional groups in place of the semi-permanent protecting groups, which functional groups are selected from the group consisting of —O-SO$_3$ groups and —O-PO$_3$ groups, and
(c) removing the permanent protecting groups and treating the nitrogen containing group to form an amine group.

24. A process as in claim 23 wherein the functional groups are —O-SO$_3$ groups.

25. A process as in claim 24 wherein the semi-permanent protecting groups are substituted at one or more carbon positions at any of carbons 4 and 6 of D-galactosamine units, and carbons 2 and 3 of uronic acid units, and wherein the permanent protecting groups are substituted at positions at any of carbons 4 and 6 of the D-galactosamine units and carbons 2 and 3 of the uronic acid units which are not substituted by the semi-permanent protecting groups.

26. The process of claim 25 wherein
(a) The nitrogen containing groups are selected from the group consisting of
 1. N$_3$,
 2. NH—lower acyl, and
 3. N-phthalimido;
(b) the protecting groups at the carboxyl are selected from the group consisting of
 1. lower alkyl, and
 2. lower aryl;
(c) the semi-permanent protecting groups are —O-lower acyl; and (d) the permanent protecting groups are —O-benzyl.

27. The process of claim 26 wherein
(a) The nitrogen containing groups are selected from the group consisting of
1. $N_3$,
2. NH—acetyl, and
3. N-phthalimido;
(b) The protecting groups which forms an ester at the carboxyl are methyl;
(c) The semi-permanent groups are —O-acetyl; and
(D) The permanent protecting groups are —O-benzyl.

28. Process as in claim 23 further comprising the step of substituting the amine group with a group selected from the group consisting of $SO_3$ and acetyl.

29. A process as in claim 27 further comprising removing the protecting groups at the carboxyl groups of the uronic acid units.

30. The process of claim 27 which further comprises salifying the $COO^{31}$ with an alkaline metal cation.

31. The process of claim 23 wherein the semi-permanent protecting groups are acetyl and hyrolysed with a strong base followed by reaction with a sulfation agent.

32. The process of claim 28 wherein the amine group is substituted with a lower acyl.

33. The process of claim 32 wherein the amine group is substituted with acetyl.

34. The process of claim 8 wherein the condensation reaction is between a halide and an OH and is carried out in a solvent medium in the presence of a catalyst.

35. The process of claim 34 wherein the solvent is an organic solvent selected from the group consisting of dichloromethane and dichloroethane and the catalyst is selected from the group consisting of a silver and a mercury salt.

36. The process of claim 35 wherein the catalyst is selected from the group consisting of silver triflouromethane sufonate, silver carbonate, silver oxide, mercuric bromide and mercuric cyanide.

37. The process of claim 3 or 4 wherein the reactive group is 1,2-O-methoxyethylidene, and the condensation is carried out in a solvent which boils above 100 degrees centigrade in the presence of a catalyst.

38. The process of claim 8 wherein the reactive group is O-lower imidoyl and the condensation reaction is carried out in the presence of a catalyst at a temperature below or equal to 0 degrees centigrade.

39. A process for selectively positioning sulfate groups or phosphate groups on a protected acid mucopolysaccharide having from 2-12 units, which protected acid mucopolysaccharide is comprised of alternating units of a first unit and a second unit wherein the first unit is selected from the group consisting of a D-galactosamine, a neutral sugar analog of D-galactosamine, and a desoxy sugar analog of D-galactosamine, and wherein the second unit is selected from the group consisting of uronic acid, a neutral sugar analog of uronic acid, and a desoxy sugar analog of uronic acid, further wherein any uronic acid is selected from the group consisting of D-glucronic acid and L-iduronic acid, the frist and second unit being linked in the manner found in chondroitin sulfate and dermatan sulfate and having at least one each as substituents of semi-permanent protecting groups, permanent protecting groups, other protecting groups which form an ester at the carboxyl groups of the uronic acid units, and nitrogen containing groups at carbon 2 of the D-galactosamine units wherein the permanent protecting groups are stable and do not migrate to other carbon positions during removal of the semi-permanent protecting groups and the introduction of functional groups, which process comprises the steps of
(a) removing the semi-permanent protecting groups,
(b) introducing functional groups in place of the semi-permanent protecting groups, which functional groups are selected from the group consisting of —O—$So_3$ groups and —O—$PO_{13}$ groups, and
(c) removing the permanent protecting groups and treating the nitrogen containing group to form an amine group.

40. A substantially pure compound of a single structure, which compound is selected from the group consisting of:

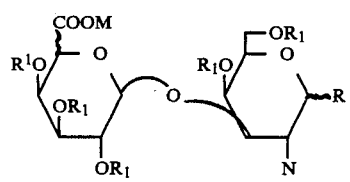

I

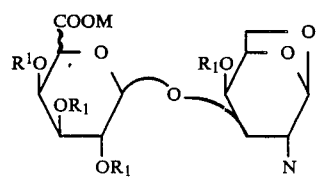

II

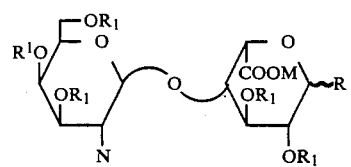

III

-continued
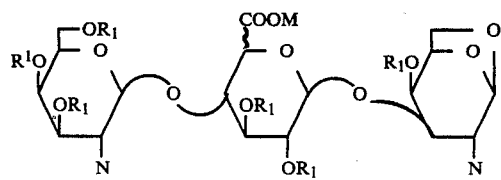           IV
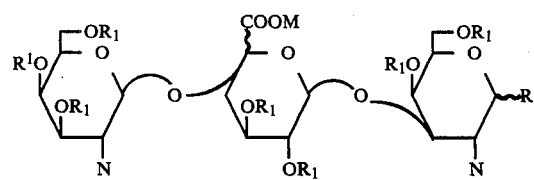           V
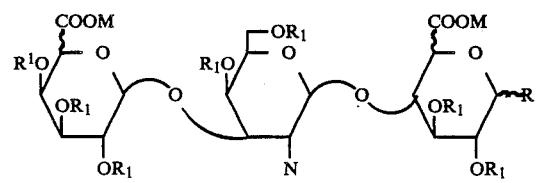           VI
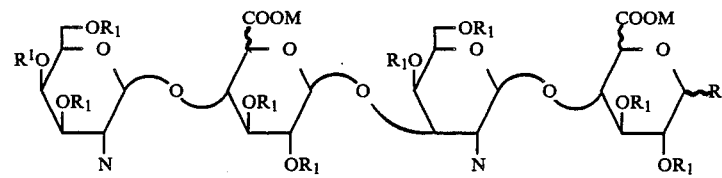           VII
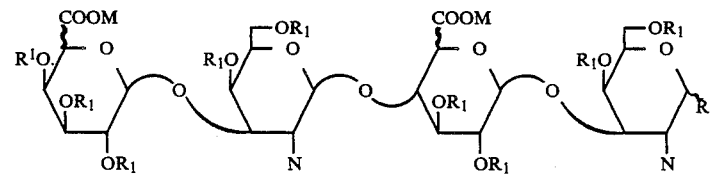           VIII
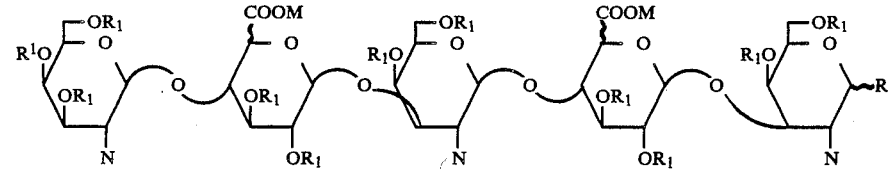           IX
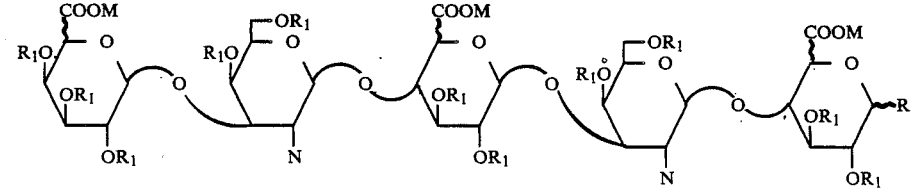           X
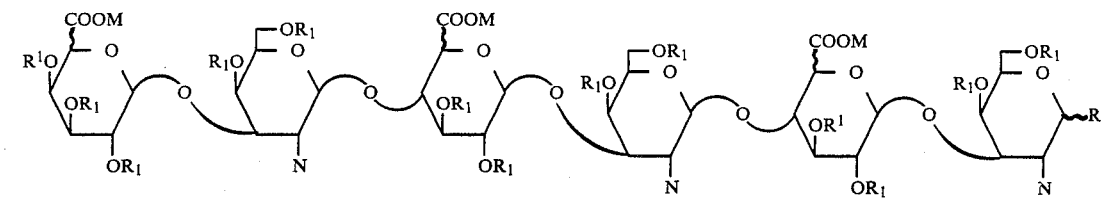           XI

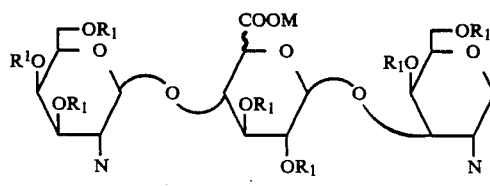 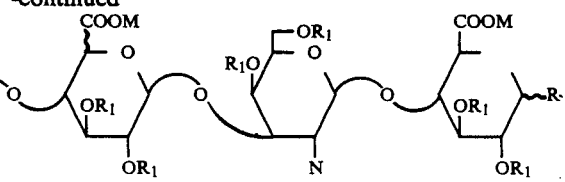

wherein
- $R_1$ substituents are not the same, and are selected from the group consisting of
  - (a) semi-permanent protecing groups, which semipermanent protecting groups are removable in the presence of permanent protecting groups, are stable during any condensation employed to obtain the compound and allow a stereospecific linkage during the condensation, and are stable during removal of any temporary groups,
  - (b) permanent protecting groups, which permanent protecting groups are stable and do not migrate to different carbon positions during removal of the semi-permanent protecting groups and the introduction of functional groups to replace the semi-permanent protecting groups, which functional groups are selected from the group consisting of $SO_3$ groups and $PO_3$ groups, and which permanent protecting groups also are removable in the presence of the functional groups, are stable during the condensation, allow a stereospecific linkage during the condensation, and are stable during removal of any temporary protecting groups,
- M is a protecting group which forms an ester at the carboxyl groups, and is stable during any condensation employed to obtain the compound,
- N is a nitrogen containing group which is treatable to form an amine, and which allows a stereospecific linkage during any condensation employed to obtain the compound,
- R is selected from the group consisting of:
  - (a) a temporary protecting group which can be removed in the presence of the other protecting groups in order to permit elongation of the compound and which is stable during any condensation employed to obtain the compound,
  - (b) a permanent protecting group,
  - (c) a reactive group which can be employed in order to perform a condensation to form a linkage as found in chondroitin sulfate and dermatan sulfate in order to elongate the compound, and which reactive group was positioned following removal of a temproary protecting group and which allows a stereospecific linkage during the condensation,
  - (d) an inert protecting group, which inert protecting group is stable during removal of the temporary protecting groups, semi-permanent protecting groups and permanent protecting groups, and
- R' is selected from the group consisting of
  - (a) a temporary protecting group,
  - (b) a permanent protecting group, and
  - (c) an OH group.

41. The substantially pure compound of claim 40 wherein the compound can be elongated and R is selected from the group consisting of a temporary protecting group and a reactive group.

42. The substantially pure compound of claim 40 wherein the compound can be elongated and R' is selected from the group consisting of a temporary protecting group and OH.

43. A substantially pure compound of a single structure, which compound is selected from the group consisting of: Compounds I, III, V, VI, VII, VIII, IX, X, XI and XII according to claim, 40 wherein
- $R_1$ substituents are not the same, and are selected from the group consisting of
  - (a) OH groups, and
  - (b) permanent protecting groups, which permanent protecting groups are stable and do not migrate to different carbon positions during removal of the semi-permanent protecting groups and the introduction of functional groups to replace the semi-permanent protecting groups, which functional groups are selected from the groups consisting of $SO_3$ groups and $PO_3$ groups, and which permanent protecting groups also are removable in the presence of the functional groups, are stable during the condensation, and allow a stereospecific linkage during any condensation employed to obtain the compound, and are stable during removal of any temporary protecting groups,
- M is a protecting group which forms an ester at the carboxyl groups, and is stable during any condensation employed to obtain the compound,
- N is a nitrogen containing group which is treatable to form an amine, and which allows a stereospecific linkage during any condensation employed to obtain the compound,
- R is selected form the group consisting of:
  - (a) a permanent protecting group,
  - (b) an inert protecting group, which inert protecting group is stable during removal of the temporary protecting groups, semi-permanent protecting groups and permanent protecting groups, and
- R' is permanent protecting group.

44. A substantially pure compound of a single structure, which compound is selected from the group consisting of: Compounds I, III, V, VI, VII, VIII, IX, X, XI and XII according to claim 40 wherein
- $R_1$ substituents are not the same, and are selected from the group consisting of
  - (a) fuctional groups which are selected from the group consisting of $SO_3$ groups and $PO_3$ groups,
  - (b) permanent protecting groups, which permanent protecting groups are stable and do not migrate to different carbon positions during removal of the semi-permanent protecting groups and the introduction of the functional groups to replace semi-permanent protecting groups, and which permanent protecting groups also are removable in the presence of the functional groups, are stable during the condensation, allow a stereospecific linkage during any condensation employed to obtain the compound, and are stable during removal of any temporary protecting groups, M is a protecting group which forms an ester at the carboxyl groups, and is stable during any condensation employed to obtain the compound, N is a nitrogen containing group which is treatable to form an amine, and which allows a stereospecific linkage during any condensation employed to obtain the compound, R is selected from the group consisting of:
  (a) a permanent protecting group,
  (b) an inert protecting group, which inert protecting group is stable during removal of the temporary protecting groups, semi-permanent protecting groups and permanent protecting groups, and R' is a permanent group.

45. A substantially pure compound of a single structure, which compound is selected from the group consisting of: Compounds I, III, V, VI, VII, VIII, IX, X, XI and XII according to claim 40 wherein $R_1$ substituents are not the same, and are selected from the group consisting of
  (a) functional groups which are selected from the group consisting of $SO_3$ groups and $PO_3$ groups, and
  (b) OH groups, M is a protecting group which forms an ester at the carboxyl groups, and is stable during any condensation employed to obtain the compound, N is the same or different and is selected from the group consisting of
  (a) an amine,
  (b) NH acetyl, and
  (c) $NHSO_3$;

R is selected from the group consisting of:
  (a) An OH group,
  (b) an inert protecting group, which inert protecting group is stable during removal of the temporary protecting groups, semi-permanent protecting groups and permanent protecting groups, and R' is OH.

46. The substantially pure compound of claim 45 wherein N is selected from the group consisting of NH acetyl and $NHSO_3$ and wherein M is removed and the compound forms an anion.

47. The substantially pure compound of any of claims 41, 42, 43, 44, 45, or 46 wherein
  (a) any nitrogen containing group is selected from the group consisting of
    1. $N_3$,
    2. NH—lower acyl, and
    3. N-phthalimido;
  (b) any protecting group at the carboxyl is selected from the group consisting of
    1. lower alkyl, and
    2. aryl;
  (c) any semi-permanent protecting group is lower acyl;
  (d) any temporary protecting group is selected from the group consisting of
    1. —O-lower acyl,
    2. O-allyl,
    2. —O-propenyl, and
    4. halogenated —O-lower acyl,
  (e) any permanent protecting group is benzyl,
  (f) any reactive group is selected from the group consisting of
    1. halogen,
    2. lower imidoyl, and
    3. an orthoester formed between the carbon 1 and carbon 2 positions where the reactive group occupies a position at carbon 1 of a uronic acid unit,
  (g) any inert protecting group is —O-lower alkyl, and
  (h) any functional group is $SO_3$.

48. The substantially pure compound of claim 47 wherein
  (a) any nitrogen containing group is selected from the group consisting of
    1. $N_3$,
    2. NH—acetyl, and
    3. N-phtalimido;
  (b) any protecting group which fomrs an ester at the carboxyl is methyl;
  (c) any semi-permanent group is acetyl;
  (d) any temporary group is selected from the group consisting of
    1. —O-acetyl,
    2. —O-benzyl,
    3. —O-allyl,
    4. —O-propenyl,
    5. monochloro-O-acetyl, and
    6. trichloro-O-acetyl;
  (e) any permanent group is benzyl;
  (f) any reactive group is selected from the group consisting of
    1. Br,
    2. Cl
    3. an orthoester having between 3 and 6 carbons, and
    4. $C(NH)CCl_3$;
  (g) any inert blocking group is an —O-lower alkyl group having between 1 and 4 carbons, and
  (h) any functional group is $SO_3$.

49. A substantially pure chondroitin sulfate fragment of a single structure comprised of 2 to 12 saccharide units.

50. A substantially pure dermatan sulfate fragment of a single structure comprised of 2–12 saccharide units.

51. A substantially pure acid mucopolysaccharide of a single structure comprised of 2to 12 altenating D-galactosamine and uronic acid units, wherein the uronic acid units are selected from the group consisting of D-glurcuronic acid and L-iduronic acid and sulfate groups are positioned at any but not all of carbons 4 and 6 of the D-galactosamine units and carbons 2 and 3 of the uronic acid units and further wherein linkage between D-galactosamine and uronic acid are of the 1–4 beta type, and linkage between L-iduronic acid and D-galactosamine are of the 1–3 alpha type, and linkages between D-glucuronic acid and D-galactosamine are of the 1–3 beta type.

52. An effective amount of oligosaccharide according to claim 46, wherein the functional group is $SO_3$, in combination with a pharmaceutically acceptable carrier.

53. A biological reagent which consists of an oligosaccharide according to claim 46.

* * * * *